US009642667B2

(12) United States Patent
Weisshaupt et al.

(10) Patent No.: US 9,642,667 B2
(45) Date of Patent: May 9, 2017

(54) SURGICAL SYSTEM FOR CONNECTING BODY TISSUE PARTS

(75) Inventors: Dieter Weisshaupt, Immendingen (DE); Christoph Rothweiler, Donaueschingen (DE); Jürgen Wegmann, Stockach (DE); Bernd Blender, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 641 days.

(21) Appl. No.: 13/696,183

(22) PCT Filed: May 4, 2011

(86) PCT No.: PCT/EP2011/057085
§ 371 (c)(1),
(2), (4) Date: Dec. 18, 2012

(87) PCT Pub. No.: WO2011/138347
PCT Pub. Date: Nov. 10, 2011

(65) Prior Publication Data
US 2013/0090645 A1     Apr. 11, 2013

(30) Foreign Application Priority Data

May 5, 2010   (DE) .................. 10 2010 020 664

(51) Int. Cl.
*A61B 18/04* (2006.01)
*A61B 17/11* (2006.01)
(Continued)

(52) U.S. Cl.
CPC .......... *A61B 18/04* (2013.01); *A61B 17/1114* (2013.01); *A61B 18/1445* (2013.01);
(Continued)

(58) Field of Classification Search
CPC . A61B 17/1114; A61B 18/04; A61B 18/1445; A61B 2017/00504;
(Continued)

(56) References Cited

U.S. PATENT DOCUMENTS 5,824,015 A   10/1998  Sawyer
5,931,165 A   8/1999   Reich et al.
(Continued)

FOREIGN PATENT DOCUMENTS

CA   2 784 111 A1    7/2011
DE   694 29 543 T2   8/2002
(Continued)

OTHER PUBLICATIONS

English translation of Japanese Office Action dated May 27, 2014 from corresponding Japanese Patent Application No. 2013-508484.
(Continued)

*Primary Examiner* — Amanda Patton
(74) *Attorney, Agent, or Firm* — Lewis Kohn & Walker LLP; David M. Kohn

(57) ABSTRACT

A surgical system that connects biological tissue includes a) a surgical instrument with two tool elements movable in relation to one another and in each case including an electrode, which electrodes, in a coming-together position of the tool elements preferably define a minimum distance from one another, lie opposite one another and face one another, and b) a medically compatible material assisting connection of the tissue.

17 Claims, 20 Drawing Sheets

(51) Int. Cl.
*A61B 18/14* (2006.01)
*A61B 17/00* (2006.01)
*A61B 18/00* (2006.01)

(52) U.S. Cl.
CPC ........... *A61B 2017/00504* (2013.01); *A61B 2017/00831* (2013.01); *A61B 2017/1132* (2013.01); *A61B 2018/00059* (2013.01); *A61B 2018/0066* (2013.01); *A61B 2018/00642* (2013.01)

(58) Field of Classification Search
CPC .. A61B 2017/00831; A61B 2017/1132; A61B 2018/0059; A61B 2018/00642; A61B 2018/0066
See application file for complete search history.

(56) References Cited

U.S. PATENT DOCUMENTS

| | | | |
|---|---|---|---|
| 6,041,260 | A | 3/2000 | Stern et al. |
| 6,656,177 | B2 * | 12/2003 | Truckai ............ A61B 18/1445 606/205 |
| 6,895,283 | B2 * | 5/2005 | Erickson ............ A61B 5/0422 607/117 |
| 8,849,414 | B2 * | 9/2014 | Lee .................. A61N 1/0553 607/115 |
| 2003/0236518 | A1 * | 12/2003 | Marchitto et al. ............ 606/27 |
| 2005/0021026 | A1 * | 1/2005 | Baily ............... 606/51 |
| 2005/0267469 | A1 | 12/2005 | Blocher |
| 2007/0208130 | A1 | 9/2007 | Sasahara et al. |
| 2009/0048589 | A1 | 2/2009 | Takashino et al. |
| 2009/0248002 | A1 | 10/2009 | Takashino et al. |
| 2011/0028971 | A1 * | 2/2011 | Takashino et al. ............ 606/49 |
| 2011/0152861 | A1 | 6/2011 | Weisshaupt et al. |
| 2012/0022531 | A1 | 1/2012 | Winter |
| 2013/0035683 | A1 | 2/2013 | Weisshaupt et al. |

FOREIGN PATENT DOCUMENTS

| | | |
|---|---|---|
| DE | 20 2005 020 505 U1 | 3/2006 |
| DE | 20 2010 013 150 U1 | 4/2011 |
| EP | 0 367 320 A1 | 5/1990 |
| EP | 1 739 149 A1 | 1/2007 |
| EP | 2 272 453 A1 | 1/2011 |
| JP | 02-126861 A | 5/1990 |
| JP | 04-220270 A | 8/1992 |
| JP | 06-007750 U | 2/1994 |
| JP | 2009-125439 | 6/2009 |
| JP | 2009-247893 | 10/2009 |
| JP | 2010-57688 | 3/2010 |
| WO | 92/14513 | 9/1992 |
| WO | 96/07355 A1 | 3/1996 |
| WO | 99/12487 | 3/1999 |
| WO | 2005/103186 A1 | 11/2005 |
| WO | 2006/044160 A2 | 4/2006 |
| WO | 2008/082444 A2 | 7/2008 |
| WO | 2009/130752 A1 | 10/2009 |
| WO | 2010/038827 | 4/2010 |
| WO | 2010/125146 A1 | 11/2010 |

OTHER PUBLICATIONS

English translation of Japanese Office Action dated Jan. 27, 2015 in corresponding Japanese Application No. 2013-508484.

Japanese Office Action dated May 13, 2016, of corresponding Japanese Application No. 2013-508484, along with an English translation.

Japanese Official Action (Notice of Rejection) dated Nov. 8, 2016, of corresponding Japanese Application No. 2015-106930, along with an English summary.

* cited by examiner

SURGICAL SYSTEM FOR CONNECTING BODY TISSUE PARTS

RELATED APPLICATIONS

This is a §371 of International Application No. PCT/EP2011/057085, with an international filing data of May 4, 2011 (WO 2011/138347 A2, published Nov. 10, 2011), which is based on German Patent Application No. 10 2010 020 664.4, filed May 5, 2010, the subject matter of which is incorporated herein by reference.

TECHNICAL FIELD

This disclosure concerns a surgical system, in particular of the nature of a surgical kit, for connecting body tissue.

BACKGROUND

For connecting body tissue, it is known, in particular hi the case of end-to-end anastomoses, to use staplers for tissue parts to be connected to one another by staples. However, the use of staplers has the disadvantage that staples are left in the patient's body.

DE 20 2005 020 505 U1 discloses biocompatible adapters in combination with adhesive compositions, in particular based on cyanoacrylate monomers, for connecting biological tissue.

A good alternative for the connection of tissue is to coagulate tissue with HF current (high-frequency current), for example, by applying an HF current to the tissue between two HF electrodes. Applying HF current has the effect of at least partially denaturing tissue proteins with, for example, triple helical collagen, a main constituent of connective tissue, being broken down into individual collagen helices. The denatured protein constituents readily allow themselves to fuse together to achieve a tissue connection. Although this process leads to satisfactory results in most cases, problems nevertheless occur with certain types of tissue, depending on the tissue composition, and they put the safety of the connection at risk and therefore lead to incalculable risks for the patient.

It could therefore be helpful to provide a surgical system to connect body tissue which allows a simple and safe connection of the tissue parts to be connected to one another and, in particular, increases the strength of the connection of tissue parts to be connected to one another in comparison with generic surgical systems.

SUMMARY

We provide a surgical system that connects biological tissue including a) a surgical instrument with two tool elements movable in relation to one another and in each case include an electrode, which electrodes, in a coming-together position of the tool elements, preferably define a minimum distance from one another, lie opposite one another and face one another, and h) medically compatible material assisting connection of the tissue.

We also provide a medically compatible material including inorganic salt additives adapted to connect human and/or animal body tissue parts with HF current application.

DETAILED DESCRIPTION

Figure 1:
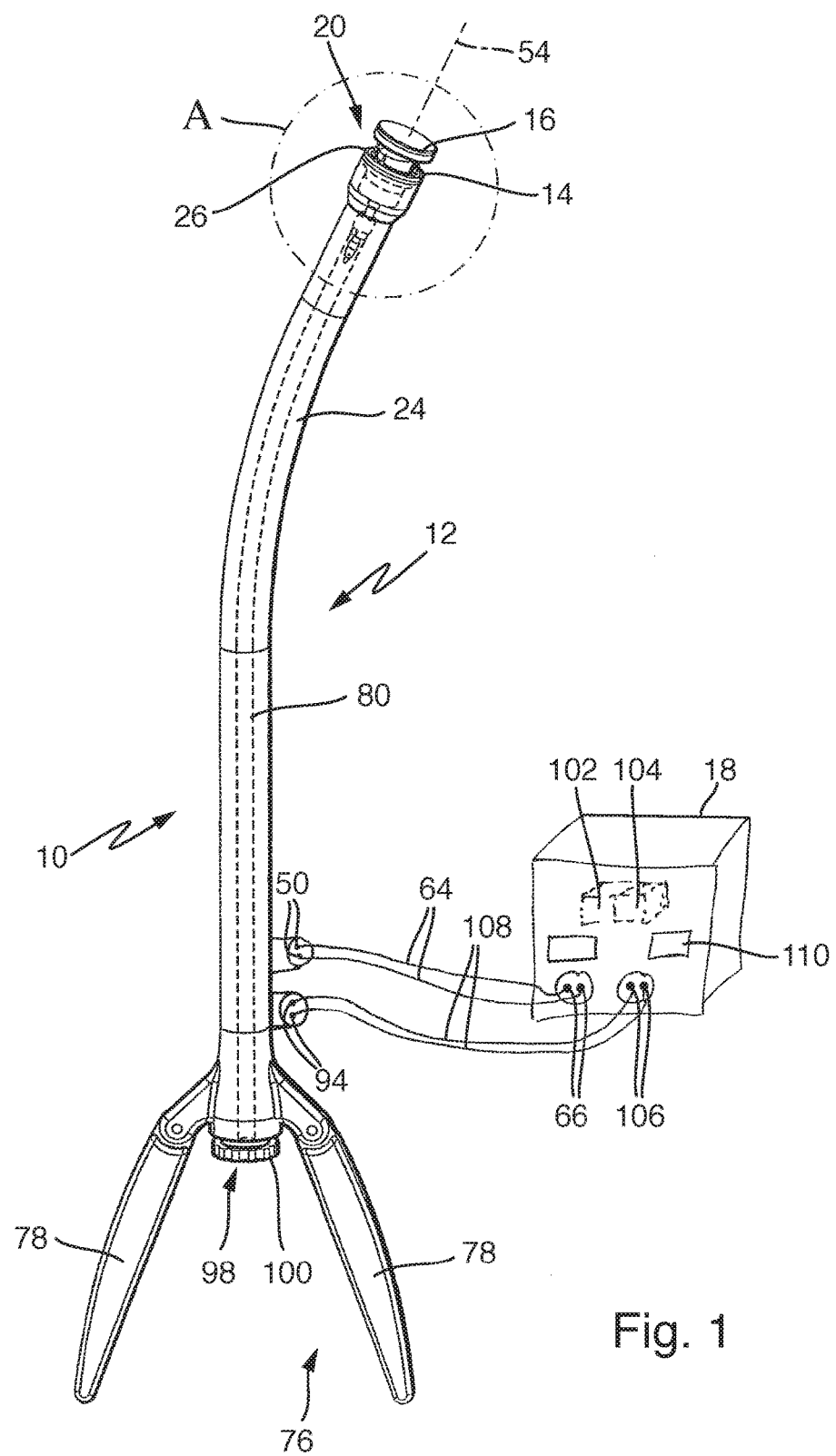
FIG. 1 shows a schematic overall view of a surgical instrument for connecting body tissue parts.

We provide a surgical system, preferably a surgical kit, for connecting biological tissue, in particular human and/or animal body tissue, comprising:
 a) a surgical instrument with two tool elements, which are movable in relation to one another and in each case comprise an electrode, preferably an HF electrode, and
 b) a medically compatible material, assisting the connection of the tissue.

In a coming-together position of the tool elements, the electrodes preferably define a minimum distance from one another, lie opposite one another and face one another.

A medically compatible material, assisting the connection of the tissue, is intended to mean a material which positively influences, in particular promotes and/or accelerates, the bringing about of a connection of tissue parts to be connected to one another, in particular human and/or animal tissue parts, as well as possibly processes that are advantageous for this, such as, for example, blood staunching, wound healing, tissue regeneration, in particular of the nature of a catalyst, and which, by medical standards, does not cause any, or any appreciable, detrimental health effects in a patient.

With particular advantage, use of the system comprising components a) and b) allows the strength, and consequently also the safety, of the connection, also referred to hereafter as sealing, or welding, of tissue parts to be connected to one another to be improved in comparison with generic surgical systems. The medically compatible material, assisting the connection of the tissue, for the sake of simplicity referred to hereafter as medically compatible material, provides additional material which can be welded together with the tissue parts to be connected. This leads to improved sealing of the welding sites. In addition, better control of the energy input into the tissue is also possible as a result of the medically compatible material, whereby the risk of detrimental effects on the tissue of concern from medical aspects can be minimized. In other words, the medically compatible material can also act as a kind of "buffer" against excess energy input. One particular advantage, however, concerns the safe connection of tissues that have a deficiency of certain tissue components, in particular proteins such as, for example, collagen, elastin or the like. The medically compatible material makes it possible for this deficiency, which puts the connection of the tissue at risk, to be compensated and nevertheless for safe care, that is risk-free or substantially risk-free for the patient, to be ensured. The medically proposed system can therefore be used universally for tissue connection. Furthermore, the medically compatible material simplifies, and in particular accelerates, the connection of tissue to be performed by the surgeon, which saves time and particularly costs.

Preferably, the medically compatible material comprises a naturally occurring material. In particular, the medically compatible material may comprise a material occurring in natural tissues, preferably natural connective tissues.

The medically compatible material may comprise a material which occurs in the tissue to be sealed itself.

The medically compatible material may be of human origin, in particular heterologous and/or autologous origin. However the medically compatible material is preferably of xenologous origin. The medically compatible material may in particular be of porcine, bovine and/or equine origin. As an alternative to or in combination with this, the material may also be of recombinant origin.

Advantageously, the medically compatible material may originate from a biological, in particular animal, tissue. The tissue is preferably selected from the group comprising the oesophagus, skin such as, for example, fascia, pericardium, ureter, tendons, ligaments and combinations thereof. With particular preference, the medically compatible material originates from an animal, in particular bovine, tissue.

The medically compatible material preferably comprises a polymer, in particular a biopolymer and/or a synthetic or technical, in particular recombinant, biopolymer or a mixture thereof. The biopolymer is preferably selected from the group comprising proteins, glycoproteins, polyamino acids, in particular polyhomoamino acids, such as, for example, lysine, polylysine, polysaccharides, lipids, glycolipids, derivatives thereof, salts thereof and combinations thereof.

With particular preference, the medically compatible material comprises a connective tissue polymer, in particular a connective tissue protein or an extracellular protein, or a mixture thereof. This is particularly advantageous, since the tissue parts to be connected to one another often constitute connective tissue. Consequently, the medically compatible material advantageously has a biological affinity with the tissue parts to be connected to one another, which in turn is advantageous in establishing the connection and achieving a nigh connecting strength. In addition, connective tissues depleted in certain components anchor account of this depletion, could otherwise not undergo any connection at all, or only to an unsatisfactory extent, can also be connected to one another with particular advantage.

The medically compatible material preferably comprises a fibrous or fiber-like protein (fibrillary protein) or a mixture of such proteins. In particular, tissue parts that are low in collagen and/or elastin can be connected to one another by the surgical system.

The medically compatible material may comprise a protein preferably selected from the group comprising collagen, gelatin, elastin, reticulin, laminin, fibronectin, fibrillin, albumin, peptide fragments thereof, subunits thereof, such as, for example, individual helices, natural polyamino acids, synthetic polyamino acids, derivatives thereof, salts thereof and combinations thereof.

It is particularly preferred if the medically compatible material comprises collagen, in particular fibrillary collagen. As already mentioned, collagen represents the main constituent of connective tissues or extracellular matrices, so that as a result a high biological affinity with the tissue parts to be connected to one another can be established. The collagen is preferably selected from the group comprising collagen of type I, II, III, V and/or VI. Collagen of type I, type III and combinations thereof, in particular collagen of type I, is particularly preferred.

The medically compatible material may also comprise an oligopeptide and/or polypeptide, in particular a natural and/or synthetic oligopeptide and/or polypeptide.

As already mentioned, it may also be provided that the medically compatible material comprises a polysaccharide. The polysaccharide may be in particular a mucopolysaccharide or glycosaminoglycan. The polysaccharide is preferably selected from the group comprising starch, amylose, amylopectin, dextran, chitosan hyaluronic acid, heparin, heparan sulphate, chondroitin-4-sulphate, chondroitin-6-sulphate, dermatan sulphate, keratan sulphate, derivatives thereof, salts thereof and combinations thereof.

The medically compatible material may comprise a cytoplasmic component, such as, for example, a polysaccharide, lipid, glycolipid, protein, such as, for example, albumin, glycoprotein or the like.

It is also preferred that the medically compatible material consists of one or more of the materials described above.

The medically compatible material is preferably formed such that it can be transferred between the two tool elements of the surgical instrument.

The medically compatible material is preferably formed such that it can be applied to a tool element area, in particular to an electrode surface, of at least one of the two tool elements.

The medically compatible material may take different forms, sizes and particularly geometries, as long as it is thereby possible together with the instrument to obtain a connection of tissue parts to be connected to one another.

The medically compatible material preferably takes the form of a formed body. In particular, the medically compatible material may take the form of a particulate formed body, such as, for example, a powder, granulate or the like.

It is more expedient, however, if the medically compatible material is formed as a fiat body or sheet-like formation, in particular as an individual layer or ply or pad. The medically compatible material may take the form of a circular formed body, oval formed body or polygonal, in particular triangular, quadrangular, in particular square or rectangular, pentagonal, hexagonal or star-shaped formed body.

With particular preference, the medically compatible material is formed as a ring-shaped formed body, plate-shaped formed body, disc-shaped formed body, strip-shaped formed body or U-shaped formed body.

Preferably, the medically compatible material has at least one opening. The at least one opening may be formed as a hole, perforation, punched clearance or the like. It is preferred if the medically compatible material, preferably in the form of a disc-shaped, in particular circular ring- or plate-shaped, formed body, has a centrally or substantially centrally arranged opening. The diameter of the opening preferably corresponds to the diameter of a preferably cylindrically formed holding member, to which the second tool element of the instrument is preferably connected.

The medically compatible material, preferably in the form of a disc-shaped, in particular circular ring- or plate-shaped, formed body, may have a number of openings, in particular holes, perforations, punched clearances or the like. The openings are preferably formed in peripheral zones or at the periphery of the medically compatible material. With preference, the openings are arranged geometrically, in particular in the form of a circle or circular ring. In addition, the medically compatible material may have a centrally or substantially centrally arranged opening of which the diameter preferably corresponds to the diameter of a preferably cylindrically formed holding member, to which the second tool element of the instrument is preferably connected.

The medically compatible material may have a porous, in particular open-porous, structure.

Advantageously, the medically compatible material may have a nonwoven structure, in particular a spray-bonded nonwoven structure, in particular may be formed as nonwoven fabric, fibrous web or felt, a foam structure, a sponge structure or a membrane structure. Possibly, the medically compatible material may also have a hybrid structure, in particular a combination of the structures mentioned in this paragraph.

The medically compatible material is preferably in a lyophilized state. Lyophilization brings about with particular advantage a shaping, and likewise dimensional stability, of the material.

With preference, the medically compatible material has a thickness, in particular a layer thickness, of 0.2 mm to 10 mm.

The medically compatible material may take the form of a gel, in particular a hydrogel, or paste.

Furthermore, the medically compatible material may be a tissue adhesive, such as, for example, a fibrin adhesive or an adhesive based on cyanoacrylates.

To increase the stability, it may also be provided that the medically compatible material is crosslinked, in particular chemically and/or physically crosslinked. For the chemical crosslinkage of the medically compatible material, crosslinking agents that are preferably selected from the group comprising aldehydes may be used, such as, for example, formaldehyde, dialdehyde, such as, for example, glutaraldehyde, polyaldehydes, such as, for example, dextran aldehyde, carbodiimides, diisocyanates, such as, for example, hexamethylene diisocyanate, salts thereof and combinations thereof. For the physical crosslinkage, the medically compatible material may, for example, be irradiated.

Particularly preferably the medically compatible material comprises additives or is provided or finished with additives. The additives may be, in particular, substances that have advantageous effects on the connection of the tissue and/or tissue healing. Suitable additives may therefore be selected, for example, from the group comprising antimicrobial substances, in particular antibiotic substances, disinfectant substances, substances conducive to wound healing, anti-inflammatory substances, cellular growth factors, cellular differentiation factors, cellular adhesion factors, cellular recruitment factors, salts thereof and combinations thereof.

It is particularly preferred if the medically compatible material is provided or finished with a salt as an additive, preferably with an inorganic salt. The addition of salts, in particular inorganic salts, to the medically compatible material allows the conductivity thereof to be increased with particular advantage. The improved conductivity in turn allows a quicker connection of tissue parts to be connected to one another to be realized by means of current, preferably HF current. However, it has additionally been found, completely surprisingly, that higher connecting strengths between the tissue parts to be connected to one another can be realized by a medically compatible material that comprises a salt, in particular an inorganic salt. The salt is preferably an alkali metal and/or an alkaline earth metal salt. The salt is preferably selected from the group comprising alkali metal halides, alkaline earth metal halides, phosphates, in particular alkali metal phosphates, alkaline earth metal phosphates and/or mixed phosphates thereof, and combinations or mixtures thereof. With further preference, the salt is selected from the group comprising sodium chloride, potassium chloride, barium chloride, magnesium chloride, calcium chloride, sodium phosphate, potassium phosphate, barium phosphate, magnesium phosphate, calcium phosphate, mixed phosphates thereof and combinations or mixtures thereof.

The additive, preferably in the form of a salt, in particular an inorganic salt, as described, for example, in the previous paragraph, may comprise a proportion of 0.01% by weight to 20% by weight, particularly 0.1% by weight to 20% by weight, in particular 0.1% by weight to 10% by weight, preferably 1% by weight to 5% by weight, with respect to the total weight, in particular dry total weight, of the medically compatible material.

The medically compatible material may be spatially or physically separate from the surgical instrument. However, it may similarly be provided that the medically compatible material is already contained in the surgical instrument. For example, the medically compatible material may be arranged between the two tool elements of the surgical instrument.

Further subject matter concerns a medically compatible material provided or supplemented with additives, in particular salts, preferably inorganic salts, for use in the connection of tissue parts to be connected to one another, in particular human and/or animal body tissue parts, by current application, preferably HF current application, to at least one of the tissue parts, preferably to both tissue parts.

The additives are preferably alkali metal and/or alkaline earth metal salts. The additives are selected in particular from the group comprising alkali metal halides, alkaline earth metal halides, phosphates, in particular alkali metal phosphates, alkaline earth metal phosphates and/or mixed phosphates thereof and combinations or mixtures thereof. The additives are preferably selected from the group comprising sodium chloride, potassium chloride, barium chloride, magnesium chloride, calcium chloride, sodium phosphate, potassium phosphate, barium phosphate, magnesium phosphate, calcium phosphate, mixed phosphates thereof and combinations or mixtures thereof.

Furthermore, it is preferred if the additives, preferably in the form of salts, comprise a proportion of 0.01% by weight to 20% by weight, particularly 0.1% by weight to 20% by weight, in particular 0.1% by weight to 10% by weight, preferably 1% by weight to 5% by weight, with respect to the total weight, in particular dry total weight, of the medically compatible material.

With respect to further features and advantages of the medically compatible material, reference is made expressly to the description so far.

Particularly preferably, at least one of the electrodes, preferably HF electrodes, is divided into at least two electrode segments, the at least two electrode segments preferably being electrically insulated from one another.

The division of at least one of the electrodes, preferably HF electrodes, into two or more electrode segments has the advantage in particular that the process parameters for connecting the tissue parts to be connected to one another can be controlled significantly more easily. The smaller the areas between which the current, in particular HF current, is used, the more easily the process parameters can be controlled. In particular, the temperature, the pressure and the tissue impedance have a major influence on the result of the connection. For example, it is also possible to set the process parameters optimally to the state of the tissue, and particularly also automatically. In particular, the electrode segments dividing the electrode, preferably HF electrode, or the electrodes, preferably HF electrodes, make it possible for the electrode, preferably HF electrode, to be supplied with current in segments, so that the tissue parts to be connected to one another can be welded or sealed to one another in segments. The sequential supply of current that is possible as a result of the segmentation of electrodes, preferably HF electrodes, allows less energy to be introduced into the tissue parts during the connecting or sealing process than in the case of comparable, unsegmented electrodes, preferably HF electrodes.

To be able to improve the controllability of the process parameters still further, it is advantageous if each of the electrodes, preferably HF electrodes, is divided into at least two electrode segments, which are electrically insulated from one another. At least two electrode segments means for the purposes of this application two or more electrode segments, that is to say in particular three, four, five, six, seven, eight, nine, ten, eleven or twelve. More than twelve electrode segments are also conceivable, however depending on the size of the tool elements, even twenty, twenty-five, thirty or forty.

At least one of the electrodes, preferably HF electrodes, is favorably divided into a plurality of electrode segments. A plurality of electrode segments should be understood as meaning more than two electrode segments, which allow still further improved controllability of the process parameters.

In the coming-together position, electrode segments lying opposite one another and facing, one another advantageously form a pair of electrode segments. Such a pair of electrode segments may, for example, be activated as a unit. In this way, in particular, local boundary conditions in the region of the two electrode segments can be optimally taken into account, in particular the temperature, pressure and/or the tissue impedance, of tissue held between the pair of electrode segments.

To be able to conduct the current, in particular HF current, in a particularly defined way for connecting the tissue from one electrode segment of the pair of electrode segments to the associated electrode segment, it is favorable if the electrode segments forming the pair of electrode segments are geometrically similar.

The function of the system can be further improved, for example, by the electrode segments forming, the pair of electrode segments being of the same size or substantially the same size. In this way, in particular, current densities can be optimally prescribed.

The at least two electrode segments can be formed particularly simply if they are of a strip-shaped or substantially strip-shaped form.

Preferably, it may be provided that each of the tool elements defines the tool element area and that the electrode, preferably HF electrode, forms part of the tool element area. This formation makes it possible to form the tool elements virtually without any projection.

The medically compatible material preferably has an area which corresponds to the tool element area of at least one of the two tool elements, in particular of both tool elements, in particular, the medically compatible material may have an area which corresponds to an electrode area of at least one of the two tool elements, in particular of both tool elements.

The tool element area is preferably planar. This makes it much easier for the instrument to be produced and cleaned.

Depending on the intended use of the surgical system, i.e. in particular dependent on the tissue parts to be connected, it may be favorable if the tool element area is of a rectangular, ring-shaped or U-shaped form. In particular, a ring-shaped or annular tool element area makes it possible to carry out end-to-end anastomoses in a simple way.

it is advantageous if the at least two electrode segments are arranged next to one another in at least two rows of electrodes. At least two rows of electrodes make it possible to produce at least two connecting lines running next to one another. This allows an improved connection and, in particular, optimum sealing of the connecting site between the tissue parts to be achieved.

To avoid short-circuits, it is also advantageous if the at least two rows of electrodes are electrically insulated from one another. Furthermore, it is thus also possible to apply a current, in particular an HF current, to the rows of electrodes separately from one another to establish a connection between the tissue parts specifically one after the other or else at the same time.

Each row of electrodes preferably comprises at least two electrode segments, which are electrically insulated from one another. Thus, at least a sequential supply of current can be realized.

Preferably, it may be provided that at least one electrode segment has a first electrode segment portion, which is part of a first row of electrodes, and a second electrode segment portion, which is part of a second row of electrodes. In this way, a two-rowed tissue connection can be created, in particular comprising or defining two connecting lines, with even better overlapping between the two connecting lines being achieved by the specially designed electrode segment portions, which results in particular in improved sealing of the tissue connection.

To be able to form desired connecting lines, it is favorable if the at least two rows of electrodes are formed in a straight line and/or curved. This means in particular that they may be formed completely in a straight line or completely curved or in a straight line in some portions and curved in some portions.

To be able to connect tissues to one another in the form of a ring, which is required in particular for end-to-end anastomoses, it is favorable if the at least two rows of electrodes are of a closed annular form.

It is advantageous if each electrode segment is connected in an electrically conducting manner to a terminal contact such that each electrode segment can be supplied with current individually as and when required. The terminal contact may in torn be connected to other terminal contacts or be connected, or able to be connected, directly to a current source.

It may also be advantageous if the electrode, preferably HF electrode, defines an electrode center line and if electrode segments that are adjacent to one another are arranged offset from one another in a direction defined by the electrode center line. The offset arrangement of the electrode segments achieves the effect of optimum overlapping in a direction transverse to the electrode center line of tissue connections or tissue connecting lines which are created by means of the electrodes, preferably HF electrodes. This allows the risk of leakages to be minimized in a specific manner.

Further preferably, it may be provided that the at least one electrode, preferably HF electrode, divided into at least two electrode segments defines an electrode length and that each of the at least two electrode segments defines a segment length, which is less than the electrode length. It can be ensured in particular by this construction that only a portion of the tissue parts to be connected to one another that is less than an overall length of the electrode, preferably HF electrode, can be connected to each electrode segment.

To improve impermeability of a connecting site between two tissue parts that is established by the surgical system, it is favorable if the sum of all the segment lengths is greater than the electrode length. This ensures at least partial overlapping of tissue connections established by the electrode segments.

To be able to connect the instrument simply and securely to a generator, preferably an HF generator (high-frequency generator), or to some other suitable current source, preferably HF current source (high-frequency current source), it is favorable if the instrument comprises at least two terminal contacts, preferably HF terminal contacts (high-frequency terminal contacts), which are connected, or able to be connected, in an electrically conducting manner to the at least two electrode segments.

To be able to accept tissue between the two tool elements, and possibly hold it during the connecting process, it is advantageous if the tool elements are formed such that they are pivotable and/or displaceable in relation to one another. Altogether, therefore, a movable arrangement of the tool elements in relation to one another is desirable.

It is favorable if the tool elements form branches mounted such that they can be pivoted or moved towards one another at distal ends or end regions. This configuration allows in particular formation of an instrument in the form of forceps, which makes it possible for the tissue parts to be connected to be held in a clamping manner between the tool elements.

Further preferable, it may be provided that the instrument has a shaft, at the distal end of which at least one of the tool elements is arranged or formed. In this way, the instrument can be formed in a particularly compact manner. Furthermore, arranging or forming at least one of the tool elements at the distal end of the shaft has the effect of increasing the overall stability of the instrument. In particular, it is thus also possible in a simple way to form one of the tool elements immovably in relation to the shaft.

It is advantageous if a first tool element comprises a peripheral area of the shaft facing in the distal direction or substantially in the distal direction of the shaft. For example, it is thus possible in a simple way for a distal end of the shaft to be pressed or held against a tissue part which is to be connected to another tissue part. Furthermore, it is also thus possible in a simple and safe way for a defined tool element area to be prescribed.

Further preferably, it may be provided that a second tool element comprises an electrode element which is movable in the direction of the shaft and is movable in the direction towards the first tool element and away from it. This configuration allows, for example, the two tool elements to be moved in relation to one another such that tissue parts to be connected to one another can be held between them in a defined way and connected to one another by correspondingly applying current, preferably applying HF current.

It is favorable if contact members, facing in the direction of the second tool element, protrude from the shaft and/or from the first tool element in the direction of the second tool element, which members can be brought into electrically conducting contact with the electrode segments of the second tool element in a tissue-connecting position and are at a distance from the electrode segments of the second tool element in a tissue-accepting position. With the contact members it is possible to contact the electrode segments of the second tool element and connect them to a current source, preferably an HF generator, by an electrically conducting connection that is provided, for example, in the shaft. Furthermore, the proposed formation has the advantage that a contact between the electrode segments of the second tool element and the contact members can only be established in the tissue-connecting position, so that in the tissue-accepting, position the electrode segments of the second tool element cannot inadvertently be supplied with current. The handling of the surgical system is thereby made even safer overall.

It is favorable if the instrument comprises an actuating device for moving the tool elements in relation to one another such that the tool elements can be moved in relation to one another in a simple way.

To improve the ease of handling the surgical instrument further, the actuating device is preferably arranged or formed at a proximal end of the instrument. For example, if the instrument has a shaft, the shall can be inserted through a body opening into the interior of the body, the tool elements then being able to be actuated in relation to one another by the actuating device, which preferably still protrudes out of the patient's body. Thus, overall, an endoscopic or minimally invasive surgical instrument can be formed in a simple manner.

The ease of handling the instrument can be improved in particular for an operator by the actuating device comprising two actuating members which are pivotable in relation to one another and are in operative connection with at least one of the tool elements to transmit an actuating force for moving the at least one tool element in relation to the other tool element. The actuating members may also be formed as only movable in relation to one another, i.e., as an alternative, for example, to a pivotable arrangement, they may also be arranged displaceably, or pivotably and displaceably, in relation to one another.

Further preferably, the instrument has a shaft, at the distal end of which at least a first of the tool elements is arranged or formed, with a second tool element being able to be brought from an operating position, in which it can be brought into the coming-together position, into a removal position, and/or vice versa, in which removal position a zone of a perpendicular projection of the second tool element onto a projection plane which runs perpendicularly in relation to the shaft direction in the region of the second tool element is smaller than in the operating position.

Being able to bring the second tool element from the operating position into the removal position in the defined way has the advantage in particular that the required free area for leading the second tool element for leading through the connecting region of the tissue parts is significantly reduced in the removal position as compared with the operating position. In particular, given a suitable configuration of the system, it can be ensured that, in the removal position, no stretching of the tissue parts that have been freshly connected to one another can take place in the region where they are connected when the instrument is removed from the tissue parts connected to one another. This has a positive effect on end-to-end, side-to-end and side-to-side anastomoses. In particular, whenever the second tool element can be brought from the removal position into the operating position again, it is also possible with the instrument to produce a number of anastomoses one after the other in a simple way without the instrument as a whole having to be removed from the tissue parts to be connected to one another, which are preferably of a tubular form.

The construction of the system can be simplified in a simple way by the second tool element being formed as a ring or plate. Furthermore, it is also possible in particular for annular, i.e., closed, electrodes to be arranged simply and securely on such second tool elements.

To transfer the second tool element from the operating position into the removal position and/or vice versa, it is favorable if the second tool element is mounted movably on a holding member. For example, the second tool element can thus be moved in relation to the holding member in a defined way, the holding member optionally itself in relation to a further part of the instrument, for example, a shaft of the same.

Particularly simple constructions for movable mountings of the second holding element on the holding member can be realized, for example, if the second tool element is mounted displaceably and/or pivotably on the holding member.

The second tool element is favorably mounted pivotably about a pivot axis, which runs transversely, in particular perpendicularly, in relation to a holding member longitudinal axis defined by the holding member. For example, a second tool element, which is in the form of a ring or plate and in the operating position defines a plane perpendicular to the holding member longitudinal axis, may thus be pivoted such that in the removal position it is inclined in relation to the plane described, in particular perpendicular thereto.

To be able to bring the second tool element into as compact a form as possible in the removal position, it is advantageous if the surgical system comprises a folding mechanism for transferring the second tool element from the operating position into the removal position. For example, a folding mechanism may be formed such that the second tool element itself in turn comprises two parts which are arranged or formed pivotably or in some other way movably in relation to one another.

To be able to bring the second tool element from the operating position into the removal position and/or vice versa in a simple way, it is favorable if the folding mechanism comprises a force transmission element for transmitting actuating force to the second tool element to transfer the same from the operating position into the removal position and/or vice versa. With the force transmission element it is possible to actuate the folding mechanism, which allows a transfer of the second tool element from the operating position into the removal position and/or vice versa.

The force transmission element is preferably arranged movably in relation to the holding member. For example, the second tool element may be brought into a desired position by the holding member, with it being possible for the folding mechanism to be actuated by the force transmission element, which can be moved in relation to the holding member.

Depending on the intended use and the configuration of the surgical system, it may be advantageous if the force transmission element and the holding member are formed such that they can be displaced and/or turned and/or screwed in relation to one another. Such an arrangement of the force transmission element and the holding member in relation to one another makes it possible to provide virtually any desired actuating mechanisms, for example, for actuating the folding mechanism.

Preferably, it may also be provided that the holding member and the force transmission element are arranged movably in relation to the shaft. For example, the shaft can thus be held by an operator and the force transmission element moved in relation to the shaft, whereby in particular the folding mechanism can be actuated to reduce the area requirement necessary for removing the second tool element. By making the holding member and the shaft movable in relation to one another, the tool elements can also be moved in relation to one another in the operating position, whereby they can be brought into a coming-together position, as small a distance apart as possible, for example, for connecting tissue, and can be moved away from one another again, for example, before transferring the instrument from the operating position into the removal position.

Further preferably, it may be advantageous if an actuating mechanism coupled to the folding mechanism and/or the force transmission element and/or the holding member is provided to actuate the folding mechanism and/or for moving the force transmission element and/or the holding member in relation to the shall. Depending on the formation of the instrument, the actuating mechanism defined in this way allows the second tool element to be brought from the operating position into the removal position and vice versa in a simple and safe way.

To facilitate and/or stabilize a movement of the second tool element and the force transmission element, it is favorable if the second tool element and the force transmission element are coupled to one another in a jointed manner by at least one articulating member. It is also conceivable to provide two, three or more articulating members.

To pivot the second tool element in relation to the holding member, it is advantageous if the at least one articulating member acts with one end on the second tool element at a point of action or articulation that is at a distance from the pivot axis. Depending on the choice of the point of action or articulation, a force required for pivoting the second tool element can thus be set.

The second tool element is advantageously in the form of two or more parts. Depending on the configuration of the parts forming the second tool element, the second tool element can thus be brought into a particularly compact form in the removal position.

Further preferably, it may be provided that the second tool element comprises at least two tool element parts, which are movable in relation to one another during the transfer from the operating position into the removal position. For example, they may be formed such that they can be displaced and/or rotated in relation to one another to reduce an area of the second tool element in the removal position in comparison with the operating position.

The surgical system can be formed particularly simply if the at least two tool element parts are pivotable in relation to one another. In particular, they can thus be folded together in a simple way.

To connect tissue parts to be connected to one another to one another by a current, it is favorable if the second tool element comprises an electrode element which is movable in the direction of the shaft and is movable in the direction towards the first tool element and away from it. In particular, the electrode element may carry an IV electrode. The electrode element itself may optionally also be of two or more parts in this way to reduce the space requirement of the second tool element in the removal position in comparison with the operating position.

Further preferably, it is advantageously provided that the instrument comprises a cutting element, preferably an HF cutting element (high-frequency cutting element), for cutting through tissue. The provision of a cutting element, which may, for example, be part of a cutting device of the instrument, allows, in particular, tissue parts that are to be connected to one another to be prepared in the desired way. For example, this may be the case if end-to-end anastomoses are created with the system, with it being possible for free ends of tubular tissue to be connected by the instrument in the form of a ring and then surplus tissue to be cut off by the cutting element or the cutting device.

The cutting element, preferably HF cutting element, preferably has a cutting edge, which defines a cutting plane inclined in relation to a longitudinal axis of the instrument, in particular in the region of the cutting element. The inclined cutting plane allows, for example, an HF current to be made to pass via the cutting element to cut through tissue. The cutting edge formed in this way is then only at a minimal distance from a counterelectrode in a small region, the counterelectrode defining a plane transverse to the longitudinal axis of the instrument. Thus, a cutting spark can be generated in a defined manner in the region of the smallest distance between the cutting element and a corresponding counterelectrode, with the cutting spark then being able to travel along the inclined cutting edge in a defined way.

To be able to carry out an annular cut easily and safely, the cutting edge is favorably of a closed annular form.

So that a current, preferably HF current, can be applied to the cutting element, preferably HF cutting element, in a defined way, it is advantageous if the instrument has a cutting terminal, preferably an HF cutting terminal, connected in an electrically conducting manner to the cutting element. In particular, in the case of such a configuration, a current for cutting through tissue can be applied to the cutting element in a defined manner, preferably independently and at a separate time from when a current is applied to the electrode segments for connecting, the tissue parts to one another.

It is advantageous if the cutting element is arranged movably in relation to at least one of the tool elements. This allows, for example, the cutting element to move in relation to the tool elements such that it cannot come into contact with the tissue parts to be connected to one another when they are connected to one another by the electrode segments formed on the tool elements. Rather, it is thus only possible after the connecting of the tissue parts, for example, to bring the cutting element into a position in which the latter can be trimmed and/or cut through completely or partially in the desired way.

To be able to apply current, preferably HF current, to the instrument in the desired way, the surgical instrument preferably comprises at least one current generator, preferably an HF current generator, which is able to be optionally connected in an electrically conducting manner to the electrodes, preferably HF electrodes, and/or the cutting element, in particular, a current that is optimum in each case for the connecting or cutting-through of tissue can thus be set.

Further preferably, it may be provided that the system comprises at least one open loop and/or closed-loop control device with a switching device for sequentially applying current, preferably HF current, to the electrode segments of at least one electrode, preferably an HF electrode. Current, preferably HF current, may optionally also be applied to a further electrode, preferably a further HF electrode, by the open-loop and/or closed-loop control device. The switching device, formed in the way described, particularly allows a current, preferably HF current, to be applied to the electrode segments of an electrode, preferably an HF electrode, one after the other, that is to say in a sequential sequence to connect the tissue parts to be connected to one another portion by portion.

It is favorable if the surgical system comprises an open-loop and/or closed-loop control device with a switching device for simultaneously applying current, preferably HF current, to at least two electrode segments of at least one electrode, preferably at least one HF electrode. In this way, the connecting or scaling process can be accelerated or carried out more quickly, since two tissue parts to be connected to one another can be connected to one another along two portions at the same time. In particular, it is also conceivable to apply a current, preferably HF current, in each case to two electrode segments simultaneously and then to further electrode segments sequentially.

To avoid short-circuits when current, preferably HF current, is applied to two electrode segments simultaneously, it is favorable if at least one further electrode segment is arranged between the at least two electrode segments.

It is favorable if the switching device is formed for switching at least one output, preferably an HF output, of the at least one current generator, preferably the at least one HF current generator. It is also possible for two, three or even more outputs, preferably HF outputs, to be provided and subjected to open-loop and closed-loop control by the switching device, for example, to apply a current, preferably HF current, of a desired strength specifically to individual electrode segments of electrodes, preferably HF electrodes.

It is advantageous if the surgical system comprises a generator, preferably an HF generator, which is able to be optionally connected in an electrically conducting manner to the electrodes, preferably HF electrodes, or the cutting element, preferably HF cutting element, and comprises the open-loop and/or closed-loop control device. In this way, a number of functions of the system can be accommodated in one unit, which improves both the production thereof and the ease with which it can be handled.

The open-loop and/or closed-loop control device is favorably formed such that the strength of a current supplied and/or the duration for which a current is supplied can be set for the individual electrode segments. In this way, process parameters, such as, for example, the temperature, pressure and/or tissue impedance, can be kept in the desired range directly or indirectly by the open-loop and/or closed-loop control device.

To avoid excessive heating of the tissue parts to be connected to one another, which would result in cells being destroyed, it is advantageous if the open-loop and/or closed-loop control device comprises a temperature measuring device for measuring an electrode segment temperature and/or a tissue temperature.

Furthermore, a method controls the surgical system wherever current, preferably HF current, is applied to at least one of the electrodes, preferably at least one of the HF electrodes, and at least one other of the at least two electrodes are left without current, and a medically compatible material, assisting the connection of the tissue, is located between the at least two electrodes.

At least one of the electrodes is preferably divided into at least two electrode segments, the two electrode segments preferably being electrically insulated from one another. Current is preferably applied to one of the at least two electrode segments, whereas at least one other of the at least two electrode segments is left without current. With such a control method, it is possible to supply current to the at least two electrode segments at least partially sequentially, i.e., one after the other. This allows current densities required for connecting tissue to be reduced, which has positive effects on process parameters, such as, for example, temperature, pressure and/or tissue impedance, and their controllability. The tissue parts to be connected to one another can in this way be connected to one another much more tolerably. By supplying appropriate current to the electrode segments, different portions of the tissue parts to be connected to one another can then be connected to one another one after the other.

To reduce the time required for connecting the tissue parts, it is favorable if at least two electrode segments are supplied with current at the same time. The segments preferably do not lie directly adjacent to one another. Short-circuits and undesired temperature increases in specific regions of tissue can thus be avoided.

Electrode segments adjacent to one another are preferably supplied with current one after the other. In this way, portions of the tissue parts to be connected to one another that are clearly and unequivocally delimited from one another can be connected to one another in a defined way.

With respect to further features and advantages of the control method, in particular with respect to the medically compatible material assisting the connection of tissue, reference is expressly made to the above description.

We also provide a process for connecting two body tissue parts, using the surgical system. The body tissue parts to be connected are preferably kept in contact with one another between the electrodes, in particular HF electrodes, with the medically compatible material, assisting the connection of tissue, being arranged between the tissue parts to be connected, in particular in the manner of a sandwich structure, and consequently likewise between the electrodes. At least one of the electrodes is preferably divided into at least two electrode segments. The electrode segments are preferably electrically insulated from one another. The body tissue parts are welded to one another, together with the medically compatible material, by means of a current, preferably by means of an HF current, along a connecting line. The welding of the body tissue pans and of the medically compatible material takes place by applying the current to at least one of the electrodes, preferably by applying the current to at least two electrode segments of at least one of the electrodes.

The proposed process offers a simple alternative to the use of staplers and obviates the need for staples, and consequently eliminates possible risks of when they are left in the patient's body. Furthermore, the medically compatible material assists, or is conducive to, the connection of tissue, whereby this can be realized more easily, and in particular more quickly. Moreover, with the medically compatible material, a greater sealing strength can be realized between the tissue parts to be connected. By the process described, two tissue parts can be connected to one another, in particular in a defined and safe way, and in particular while improving or increasing the strength of the connection, without destroying body cells.

To avoid short-circuits and detrimental effects on the cells, it is advantageous if current is applied to the at least two electrode segments one after the other.

It is favorable if the electrodes prescribe the connecting line so that an operator can connect the two tissue parts to one another along a defined connecting line. It is thereby possible already when an instrument is placed on the body tissue parts that are to be connected to one another to define along which line the parts are set to be connected to one another.

With respect to further features and advantages of the process, in particular with respect to the medically compatible material assisting the connection of tissue, reference is likewise expressly made to the above description.

The following description of preferred examples serves for a more detailed explanation in conjunction with the Drawings.

EXAMPLES

1. Preparation of Collagen Suspensions

To prepare collagen suspensions, 66 g of collagen were allowed to swell in 1320 g of ultrapure water (MilliQ water from the company Millipor, Germany) and 8 g of glacial acetic acid. The swollen collagen was subsequently suspended for 20 minutes in a solvent mixture of 2310 g of ultrapure water and 330 g of isopropanol.

2. Preparation of Collagen Nonwovens

Different amounts by weight (cf. in this respect Table 1 below) of the suspensions prepared in Example 1 were respectively poured into lyophilization dishes (dish size: 21×29 cm) and subsequently lyophilized. Rectangular collagen sheets were obtained as products. Depending on the amount of suspension poured on, the thickness and dry amount of collagen per unit area varied.

TABLE 1

| Designation | Filling weight of the dishes [g] | Average thickness of the collagen sheets [mm] | Dry weight of collagen per unit area [mg/cm$^2$] |
| --- | --- | --- | --- |
| V200 | 200 | 2.6 | 7.6 |
| V250 | 250 | 3.3 | 9.5 |
| V300 | 300 | 4 | 11.4 |
| V350 | 350 | 4.7 | 13.3 |
| V400 | 400 | 5.4 | 15.2 |
| V450 | 450 | 6 | 17.1 |

The suspensions may also be lyophilized directly in devices which have a cavity corresponding to the final shape (disc, ring or the like) and final size.

3. Preparation of Collagen Membranes

Different amounts by weight (cf. in this respect Table 2 below) of the suspensions prepared in Example 1 were poured into lyophilization dishes (dish size: 21×29 cm) and subsequently dried in a drying cabinet at 37° C. The lyophilized products may in principle be dried at temperatures between 25 and 40° C., in particular 35 and 40° C. Rectangular collagen membranes were obtained as products.

Depending on the amount of suspension poured on, the thickness and dry amount of collagen per unit area varied.

TABLE 2

| Designation | Filling weight of the dishes [g] | Average thickness of the collagen sheets [μm] | Dry weight of collagen per unit area [mg/cm$^2$] |
|---|---|---|---|
| M200 | 200 | 78 | 7.6 |
| M250 | 250 | 85 | 9.5 |
| M300 | 300 | 90 | 11.4 |
| M350 | 350 | 105 | 13.3 |
| M400 | 400 | 120 | 15.2 |
| M450 | 450 | 150 | 17.1 |

Alternatively, the collagen suspensions may also be dried in devices which have a cavity corresponding to the final shape (disc, ring or the like) and final size.

4. Addition of Inorganic Salts to Collagen Membranes

Defined amounts of sodium chloride (cf. in this respect Table 3 below) were added to the collagen suspensions prepared in accordance with Example 1.

TABLE 3

| Designation | Addition of NaCl per 350 g of suspension [mg] | Average thickness of the collagen sheets [μm] | Dry weight of collagen per unit area [mg/cm$^2$] |
|---|---|---|---|
| M350 S 0025 | 88 | 90 | 13.3 |
| M350 S 005 | 175 | 90 | 13.3 |
| M350 S 010 | 350 | 90 | 13.3 |
| M350 S 015 | 525 | 90 | 13.3 |
| M350 S 020 | 700 | 90 | 13.3 |
| M350 S 050 | 1750 | 90 | 13.3 |
| M350 S 100 | 7000 | 90 | 13.3 |
| M350 S 200 | 14000 | 90 | 13.3 |
| M350 S 300 | 21000 | 90 | 13.3 |

5. Addition of Inorganic Salts to Collagen Fleeces

Defined amounts of sodium chloride (cf. in this respect Table 4 below) were added to the collagen suspensions prepared according to Example 1 before a final lyophilization,

TABLE 4

| Designation | Addition of NaCl per 350 g of suspension [mg] | Average thickness of the collagen sheets [mm] | Dry weight of collagen per unit area [mg/cm$^2$] |
|---|---|---|---|
| V350 S 0025 | 88 | 4.7 | 13.3 |
| M350 S 005 | 175 | 4.7 | 13.3 |
| M350 S 010 | 350 | 4.7 | 13.3 |
| M350 S 015 | 525 | 4.7 | 13.3 |
| M350 S 020 | 700 | 4.7 | 13.3 |
| M350 S 050 | 1750 | 4.7 | 13.3 |
| M350 S 100 | 7000 | 2.4 | 13.3 |

6. Connecting Pieces of Intestine by Means of the Collagen Membranes and Fleeces Prepared According to Examples 4 and 5

On the basis of a series of tests with a small intestine (pig), the differences which occur when sealing with and without collagen were presented. The peeling forces between the connected intestine segments were determined with a spring balance. For this, the intestine segments were cut into pieces of the same size. Subsequently, a "sandwich" of an intestine segment, collagen pad (collagen membrane or collagen nonwoven) and again an intestine segment was made. When doing so, it was ensured that the outer sides of the intestine segments were facing the collagen pad. The electrode area via which the energy required for the welding was introduced into the tissue corresponded in all cases to an area of 50 mm$^2$. The time for which the energy acted was controlled by a generator. After completion of the process, the intestine segments were clamped in clamps and pulled apart. The force required to tear the welded seam apart was determined by a spring balance.

TABLE 5

| Designation of the sample | Peeling force |
|---|---|
| None | 100.00% |
| M200 | 110.23% |
| M300 | 131.06% |
| M400 | 112.12% |

TABLE 6

| Designation of the sample | Peeling force |
|---|---|
| M350 | 100.00% |
| M350 S0025 | 114.52% |
| M350 S005 | 120.97% |
| M350 S010 | 131.45% |
| M350 S015 | 141.13% |

TABLE 7

| Designation of the sample | Peeling force |
|---|---|
| None | 100.00% |
| V200 | 217.14% |
| V300 | 300.00% |
| V400 | 157.14% |

TABLE 8

| Designation of the sample | Peeling force |
|---|---|
| V300 | 100.00% |
| V300 S020 | 112.50% |

The dry weight of collagen, with respect to the area of the collagen pads, was 5 to 20 mg/cm$^2$, preferably 8 to 17 mg/cm$^2$, particularly preferably 10 to 15 mg/cm$^2$.

The salt content in the membranes was 0.01 to 3% by weight, preferably 0.025 to 1% by weight, particularly preferably 0.1 to 5% by weight, with respect to the weight of poured-on suspension.

The results presented in Tables 5 to 8 make it clear that the strength of the sealing of the tissue can be increased significantly by the additional use of a collagen pad. This is of decisive advantage in particular when sealing tissues that are low in collagen. In addition, it has surprisingly been found that the addition of inorganic salts not only leads to an increase in the conductivity of collagen pads, and consequently to quicker sealing of the tissue Parts to be connected to one another, but also to an additional increase in the strength of the connecting or sealing site.

Sealing Tests Assisted by Collagen

Sealing of small intestine and large intestine was conducted. To this end, collagen was used as medically compatible material for assisting sealing. Afterwards, the sealed samples were tested in respect of their peeling resistance.

Small intestine from a pig was used. The pig was butchered at the day at which the tests were performed. The small intestine was cleaned subsequent to its isolation. Then, the tissue was cooled and transported to the place where the tests were performed. The small intestine being contained in a plastic bag was stored in a refrigerator.

Further, large intestine (colon transversum) from a pig was used. The large intestine was prepared and transported in the same manner as the small intestine mentioned in the preceding paragraph.

Collagen preparations of bovine origin having different proportions of NaCl were used as medically compatible material to assist sealing. The salt proportions relate to the wet weight of the manufacturing process of the collagen preparations. For the dry preparations, a multiplication factor of about 40 has to be applied in respect of NaCl proportion.

The following concentrations were applied for the Examples:

| Wet | Dry |
| --- | --- |
| 0% NaCl | ⇒ 0% NaCl in TM |
| 0.025% NaCl | ⇒ 1% NaCl in TM |
| 0.05% NaCl | ⇒ 2% NaCl in TM |
| 0.10% NaCl | ⇒ 4% NaCl in TM |
| 0.15% NaCl | ⇒ 6% NaCl in TM |
| 0.20% NaCl | ⇒ 8% NaCl in TM |
| 0.25% NaCl | ⇒ 10% NaCl in TM |

The dry weight was about 5 kg/m$^2$, yielding a dry area weight of about 125 g/m$^2$.

The small intestine was cut and opened at the beginning of the fatty tissue. Afterwards, the small intestine was cut to a rectangle having the dimensions 30×70 mm.

Each collagen preparation Was placed between two of such tissue pieces. Thereafter, the samples prepared in this manner were sealed at the short edge thereof using a system consisting of a high-frequency generator and electrodes. After sealing, 7 mm broad pieces were cut out of the sealing portion.

Then, peeling forces of the pieces were measured. To this end, the intestine was clamped at the non-sealed ends using clamping jaws and was pulled apart using a tension testing machine. The pull rate applied was 50 mm/min. The peeling resistance was measured taking into consideration the measured forces and the width of the samples.

For control, peel resistance of small intestine and large intestine without the usage of collagen was also measured. The results thereof were standardized as 100%.

TABLE 9

Test results of small intestine

| Test | Peel resistance [%] |
| --- | --- |
| Small intestine without collagen | 100% |
| Small intestine with collagen and without NaCl | 186% |
| Small intestine with collagen and 0.025% NaCl | 206% |
| Small intestine with collagen and 0.05% NaCl | 294% |

TABLE 10

Tests of large intestine

| Test | Peel resistance |
| --- | --- |
| Large intestine without collagen | 100% |
| Large intestine with collagen and without NaCl | 675% |

The results displayed in the Tables 9 and 10 confirm that tissue sealing of small intestine and large intestine may be considerably enhanced using collagen, in particular finished with NaCl, as a medically compatible material for assisting sealing. More specifically 2.94 fold enhancement could be achieved in respect of small intestine and 6.75 fold enhancement could be obtained in respect of large intestine in comparison to sealing without collagen.

Turning now to the Drawings, in FIG. 1, a surgical system for connecting body tissue is schematically represented and designated overall by the reference sign 10. It comprises a surgical instrument 12 with two tool elements 14 and 16, which are movable in relation to one another. Furthermore, the system 10 comprises a current generator in the form of an HF current generator 18, which can be connected to the instrument 12 in a way described in more detail below.

The tool elements 14 and 16 form part of a connecting device, provided overall with the reference sign 20, for connecting body tissue. The first tool element 14 comprises a peripheral area 22, facing in the distal direction, of an elongated, sleeve-shaped shaft 24 of the instrument 12. Consequently, the first tool element is arranged or formed at a distal end 26 of the instrument 12.

The first tool element 14 comprises an HF electrode 28. It is divided into at least two electrode segments 30, in the case of the example that is schematically represented in FIGS. 2 to 5 into four electrode segments 30, which are electrically insulated from one another. The electrode segments 30 are of a strip-shaped or substantially strip-shaped form. The first tool element 14 defines a tool element area 32 such that the HF electrode 28 forms part of the same. Altogether, the tool element area 32 is of a planar and annular form.

The four electrode segments 30 define two rows of electrodes 34 and 36. Each row of electrodes in each case comprises part of the four electrode segments 30. As can be seen, for example, in FIG. 5, each electrode segment 30 has a first electrode segment portion 38, which forms part of the first row of electrodes 34, and a second electrode segment portion 40, which forms pan of the second row of electrodes 36. The two rows of electrodes 34 and 36 are formed overall in a curved manner, the electrode segment portions 38 and 40 in each case defining electrically conductive circular ring portions. Altogether, the at least two rows of electrodes which are defined by in each case four electrode segment portions 38 and 40, respectively, are of a closed and annular form. To be able to contact the electrode segments 30 in the desired way, each electrode segment 30 is connected in an electrically conducting manner to a terminal contact 42, which is arranged in a connecting region between the electrode segment portions 38, 40.

The HF electrode 28 defines an electrode center line 44, running between the electrode segment portions 38 and 40. Electrode segments 30 that are adjacent to one another are therefore arranged offset from one another in a direction defined by the electrode center line 44. Altogether, the HF electrode 28 divided into four electrode segments 30 defines an electrode length 46, each of the four electrode segments

30 defining a segment length 48, which is less than the electrode length 46. As represented by way of example in FIG. 5, the electrode segments 30 extend over an angular range of approximately 140° and thereby have a length which corresponds approximately to 40% of the electrode length 46. Consequently, however, the sum of all the segment lengths 48 is also greater than the electrode length 46 by approximately a factor of 1.6.

Arranged in the region of a proximal end of the shaft 24 are HF terminal contacts 50, which are connected in an electrically conducting manner, for example, by way of lines running in the shaft, to the electrode segments 30. The number of HF terminal contacts 50 corresponds to the number of electrode segments 30, that is to say four HF terminal contacts 50 for the four electrode segments 30 of the first tool element 14.

The second tool element 16 is substantially in the form of a disc and comprises an electrode element 52, which is movable in the direction towards the first tool element 14 and away from it, to be precise parallel to a longitudinal axis 54 of the shaft 24 in the region of the tool elements 14, 16 which defines a shaft direction 56. The tool elements 14, 16 are arranged displaceably in relation to one another, i.e., a distance 58 between the tool element area 32 of the tool element 14 and a tool element area 60 of the second tool element 16 is variable.

The electrode element 52 comprises an HF electrode 29, which corresponds in its construction to the HF electrode 28. This means that it likewise comprises four electrode segments 31, which do not protrude beyond the tool element area 60. Two rows of electrodes 35 and 37 are likewise defined, first electrode segment portions 39 defining the row of electrodes 35 and second electrode segment portions 41 defining the row of electrodes 37. Terminal contacts 43 are likewise provided, in each case connecting an electrode segment portion 39 in a conducting manner to an electrode segment portion 41 to form an electrode segment 31. The HF electrodes 28 and 29 are formed mirror-symmetrically in relation to a mirror plane running perpendicularly to the longitudinal axis 54 between the tool element areas 32 and 60, in this way, pairs of electrode segments 62 are defined by in each case an electrode segment 30 and the corresponding, opposite electrode segment 31. Altogether, the example represented in FIGS. 1 to 5 consequently comprises four pairs of electrode segments 62. The electrode segments 30, 31 are not only geometrically similar, but also of the same size or substantially the same size.

Figure 4:
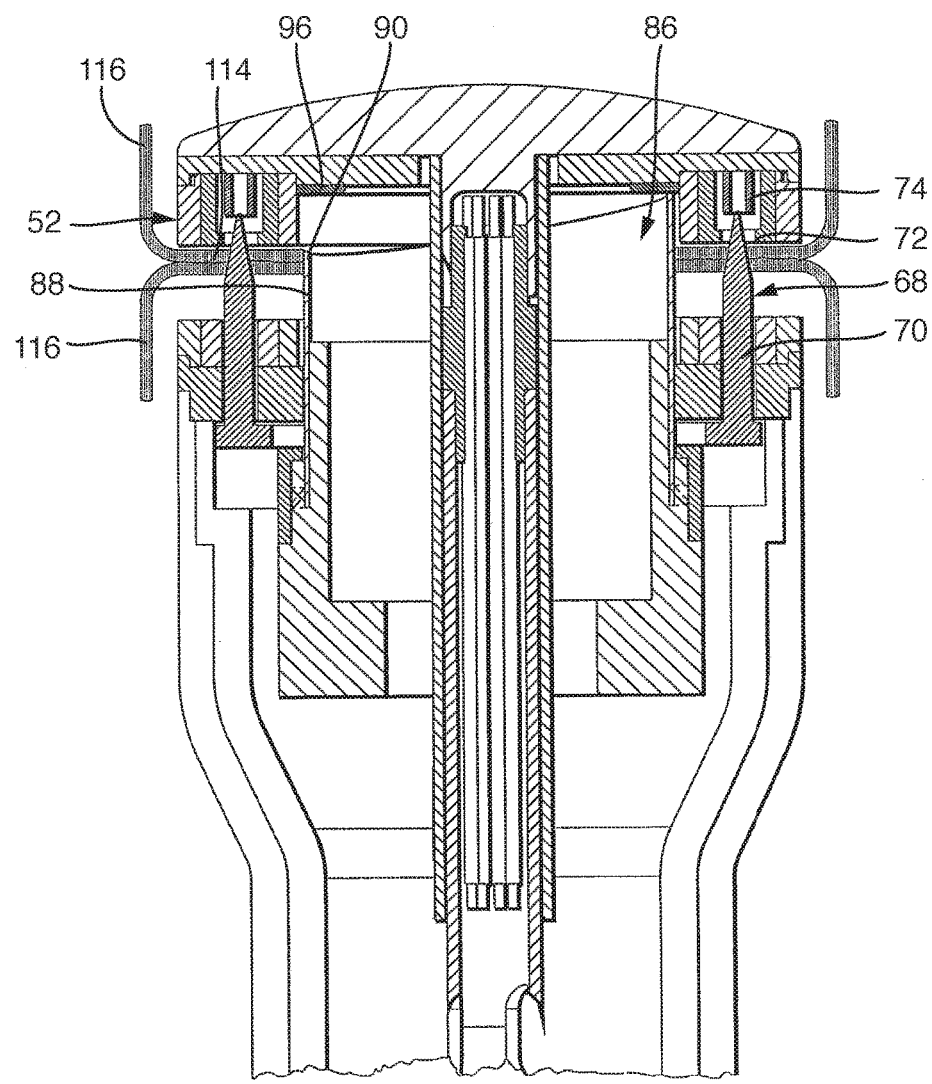
FIG. 4 shows a view analogous to FIG. 3 when welding the tissue parts for producing an end-to-end anastomosis.
Figure 5:
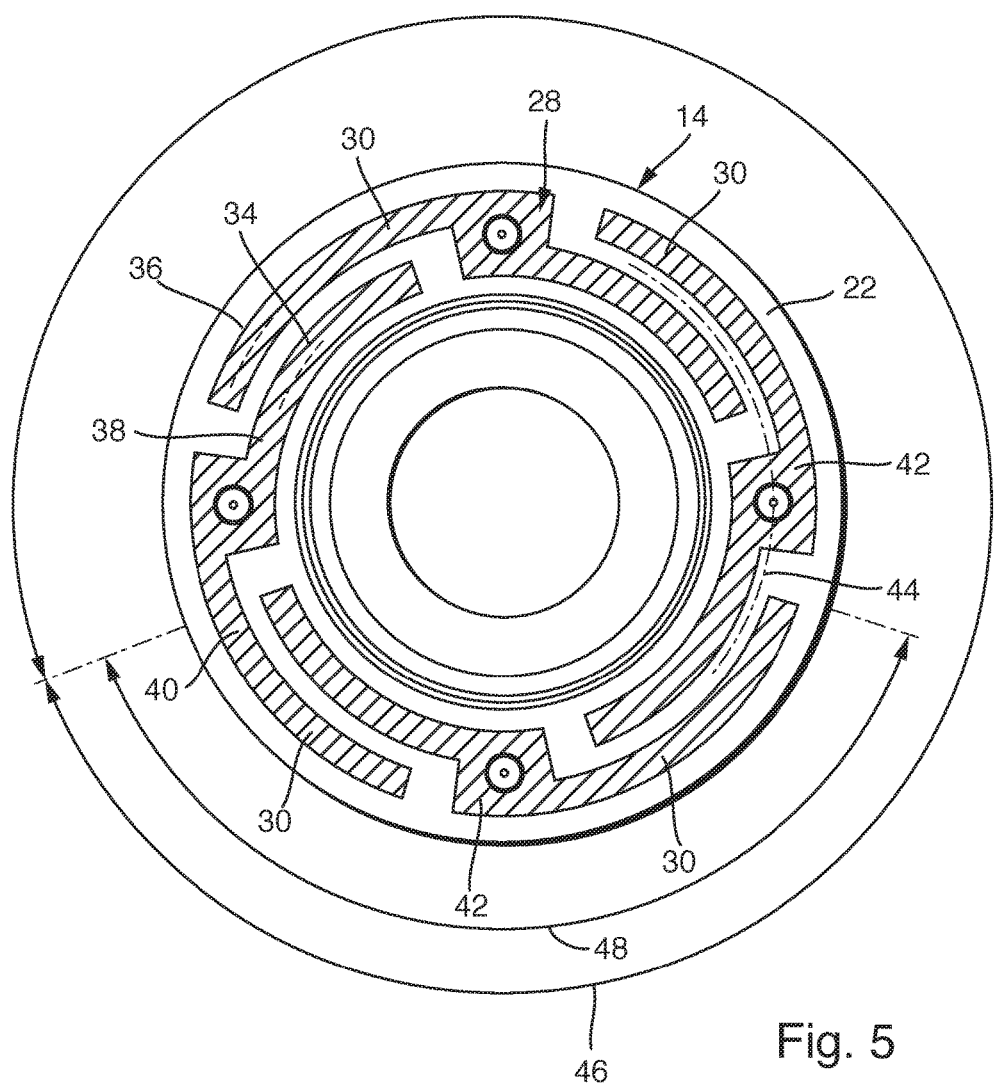
FIG. 5 shows a plan view of a tool element area with an HF electrode divided into four electrode segments.

In a coming-together position of the tool elements 14, 16, the HF electrodes 28, 29 define a minimum distance 58 from one another. The corning-together position is schematically represented in FIG. 4. In the coming-together position, the HF electrodes 28 and 29 lie opposite one another and face one another.

The electrode segments 31 are able to be connected in an electrically conducting manner to four more HF terminal contacts 50, only two of which are represented in FIG. 1 for the sake of overall clarity. The HF terminal contacts 50 can be connected by corresponding connecting lines 64 to corresponding contacts 66 of the HF current generator 18. As already explained, the HF terminal contacts 50 are directly connected in an electrically conducting manner to the electrode segments 30. To be able to connect the HF terminal contacts 50 to the electrode segments 31, contact members 68, facing in the direction of the second tool element 16, are arranged in a protruding, manner on the shaft 24 or on the first tool element 14 and have a short cylindrical portion 70 and a conical portion 72, defining a free end. In a tissue-connecting position, as schematically represented, for example, in FIG. 4, that is to say in a position in which the tool elements 14 and 16 are in the coming-together position, the free ends of the portions 72 of the contact members 68 protrude into corresponding bush-shaped receptacles 74 of the electrode element 52 and are in electrically conducting contact with them. The contact members 68 in turn are connected along the shaft 24 to the HF terminal contacts 50 by way of electrical lines that are not represented. The receptacles 74 are in turn in electrically conducting connection with the terminal contacts 43. In this way, an electrically conducting contact between the HF terminal contacts 50 and the electrode segments 31 can also be established in the coming-together or tissue-connecting position.

It goes without saying that the contact members 68, which pass through the electrode segments 30 in the region of the terminal contacts 42 thereof, are insulated from the latter, so that no shot-circuits can occur. For this purpose, the portions 70 of the contact members 68 are preferably provided with an electrically insulating coating or sheath.

To be able to move the tool elements 14, 16 of the instrument 12 in relation to one another, an actuating device 76 is arranged at a proximal end or end region of the instrument 12. The actuating device 76 comprises two actuating members 78, which are pivotable in relation to one another and movably coupled to a force transmission member 80 movably mounted in the interior of the shaft so that the force transmission member can be moved in the distal or proximal direction as a result of a pivoting movement of the actuating members 78.

Figure 2:
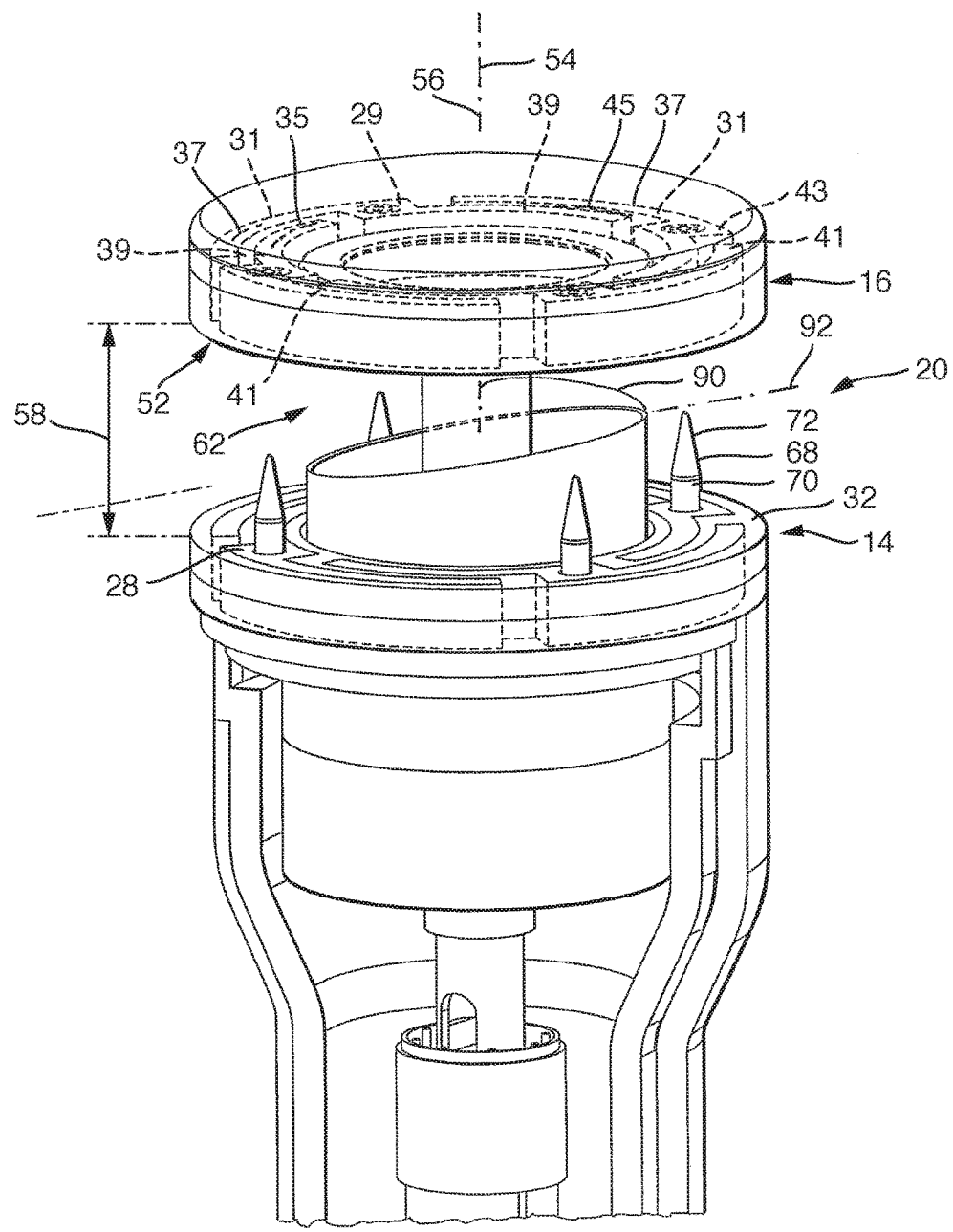
FIG. 2 shows an enlarged, perspective, partially sectioned and broken-through view of the region A in FIG. 1.
Figure 3:
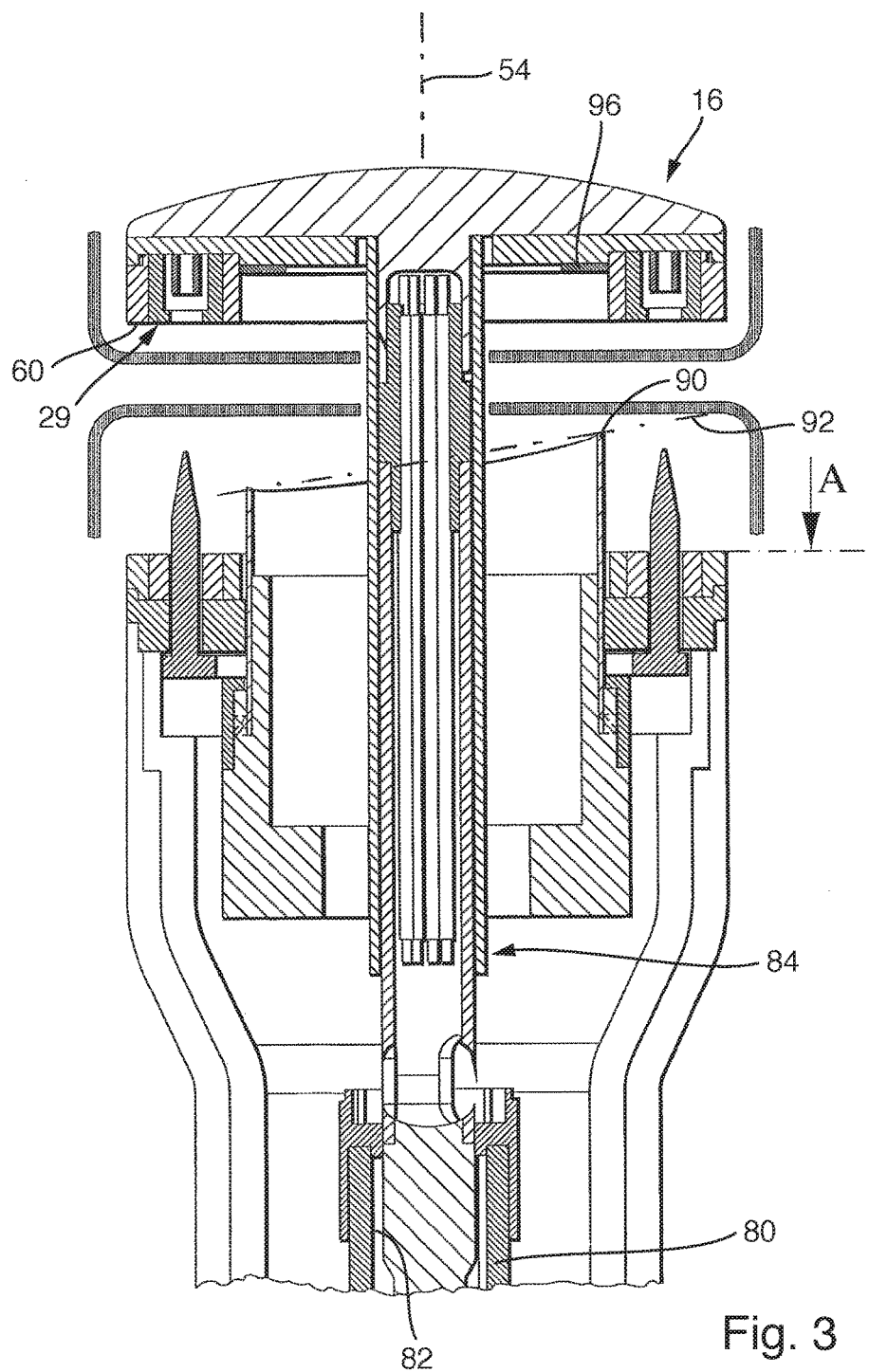
FIG. 3 shows a longitudinal sectional view of the instrument from FIG. 1 in the region A before the connecting of two tubular tissue parts.

The force transmission member 80 defines at its distal end a receptacle 82 in the form of a blind hole, into which a holding member 84 can be inserted with a first free end and can be fixed in the receptacle 82. The second free end of the substantially rod-shaped holding member 84 is immovably connected to the second tool element 16. In this way, the second tool element 16 can be moved away from the first tool element 14 as a result of a displacement of the force transmission member 80 in the distal direction. The instrument 12 is preferably formed such that the second tool element 16 can be brought from a tissue-accepting position, as schematically represented in FIGS. 2 and 3 and in which the tool elements 14, 16 are at a maximum distance 58 from one another, into the coming-together or tissue-connecting position, by pivoting the actuating members 78 towards one another, which results in a movement of the force transmission member 80 in the proximal direction.

Furthermore, the instrument 12 comprises a cutting device 86 for cutting through tissue. The cutting device comprises a cutting element 88 with a closed annular cutting edge 90. The cutting edge 90 defines a cutting plane 92, which is inclined in relation to the longitudinal axis 54 of the instrument 12. The cutting plane 92 is inclined by about 10° with respect to a reference plane which runs perpendicularly to the longitudinal axis 54 and parallel to the tool element areas 32 and 33. Provided on the shaft 24 on the proximal side is a further HF cutting terminal 94, which in a variant of the instrument 12 is connected in an electrically conducting manner to the cutting element 88. Consequently, for example, a monopolar connecting device 86 can be realized. A bipolar cutting device 86 is realized, for example, by arranging opposite the cutting edge 90, on the second tool element 16, an annular electrode 96, which is connected to a further HF cutting terminal 94 by way of an electrically conducting connection not represented in any more detail, which, for example, runs through the force transmission member 80 in a way not represented.

The cutting element 88 is preferably mounted displaceably in relation to both tool elements 14, 16. The rutting edge 90, formed concentrically around the longitudinal axis 54, can thus be displaced in relation to the HF electrodes 28 and 29. For actuating the cutting device 86, a cutting actuating device 98 is provided, with an actuating member 100 protruding from the proximal end of the instrument. This actuating member is mechanically coupled to the cutting element 88 by way of a mechanism not represented, for example, a further force transmission member running in the interior of the shaft 24, so that the cutting element 88 is also moved as a result of a movement of the actuating member 100. The actuating member 100 is preferably arranged displaceably and rotatably in relation to the shaft 24, so that the cutting, element 88 can not only be displaced parallel to the longitudinal axis 54 but can also be turned in relation to it.

To be able to apply an HF current to the electrode segments 30, 31 in any desired way, an open-loop and/or closed-loop control device 102 with a switching device 104 is provided. The open-loop and/or closed-loop control device 102 is preferably arranged in a housing of the HF current generator 18 and forms part of the same. The switching device 104 is formed in particular for applying an HF current sequentially to the electrode segments 30, 31. The switching device 104 serves in particular for activating the contacts 66 and further contacts 106, which are able to be connected to the HF cutting terminals 94 of the instrument 12 via further connecting lines 108. In this way, the cutting device 86 can be operated in a monopolar or bipolar manner with the HF current generator 16. Dispensing entirely with supplying current to the cutting device 86 allows it also to be used purely mechanically for cutting through tissue, to be precise by the preferably sharpened cutting edge 90.

The switching device 104 may also be formed such that an HF current can be applied simultaneously to at least two electrode segments 30, 31 of an HF electrode 28, 29. It is in this case favorable if, between two electrode segments 30, 31 to which HF current is applied simultaneously there is arranged in each case a further electrode segment 30, 31, which however is then without current. For example, in this way the electrode segments 30 lying opposite one another of the HF electrode 28 represented in FIG. 5 could be supplied with current simultaneously, the two other electrode segments 30 then remaining without current.

To be able to set the strength of a current supplied and/or the duration for which a current is supplied to the individual electrode segments 30, 31 individually, the open-loop and/or closed-loop control device 102 is formed to comprise a setting device 110. With the setting device 110, it is then possible, for example, for the strength and/or frequency of the HF current to be set, and similarly the duration for which the current is supplied. Furthermore, the setting device 110 may optionally also be formed to be able to set current supplying sequences individually.

Furthermore, the open-loop and/or closed-loop control device 102 preferably comprises a temperature measuring device 112 for measuring an electrode segment temperature and/or a tissue temperature. The temperature measuring device 112 serves in particular for delivering to the open-loop and/or closed-loop control device 102 the controlled variable required for automatically controlling a supply of current to the HF electrodes 28, 29, that is a temperature of the tissue, for example, indirectly by a temperature measurement of the electrode segments 30, 31. For example, electrode segments 30, 31 without current may serve as measuring contacts for recording the temperature by means of a tissue impedance measurement. In this way it can be ensured that the temperature required for connecting the tissue is achieved in the desired way and with great precision by supplying an appropriate current to the HF electrodes 28, 29, but undesired overheating of the tissue parts to be connected to one another is avoided.

With the surgical system 10 described above, tubular tissue parts 116 in particular can be connected directly to one another, by being welded or sealed to one another by HF current being applied. To be specific, the following procedure is thereby followed, for example:

To produce an end-to-end anastomosis of two tubular tissue parts 116, as required, for example, after an intestine operation in which a piece of intestine is cut out, free ends of the tissue parts 116 are brought together, so that they are lying with their free ends facing in the direction of the longitudinal axis and flat against one another in an annular manner, as represented by way of example in FIGS. 3 and 4. The free ends are then located between the two tool elements 14, 16, so that the tissue parts 116 can be held against one another in a clamping manner between the tool elements 14, 16 in the tissue-accepting position.

The tool elements 14, 16 are then moved towards one another into the tissue-connecting position, so that the electrode segments 31 are also connected in an electrically conducting manner to the HF terminal contacts 50 in the way described above. To weld the tissue parts 116, an HF current is then preferably applied to individual pairs of electrode segments 62, then flows via the portions of tissue parts held between the tool elements 14, 16 and heats them. The heating causes a change in the tissue parts, in particular in the cells contained therein, such that the tissue parts 116 bond to one another. The connecting process is preferably carried out such that current is only ever supplied simultaneously to one pair of electrode segments 62, in particular in a sequential sequence, in this way, an annular connecting line 114 is produced, prescribed substantially by the HF electrodes 28, 29 or the electrode center lines 44, 45 thereof.

The fact that an HF current is not applied to the entire HF electrodes 28, 29 means that the temperature for connecting the tissue parts 116 can be kept under control much better and destruction of the cells can be prevented. Current is preferably supplied to the electrode segments 30, 31 one after the other, that is to say sequentially, so that the tissue parts 116 are welded to one another step by step along the connecting line 114. The two-rowed arrangement of the electrode segment portions 38, 39, 40 and 41 also has the effect of establishing a double connection between the tissue parts 116, which can ensure optimum sealing and a durable, stable connection of the tissue parts 116 to one another.

As an alternative to sequentially supplying current, it is also possible, as already indicated above, for current to be supplied simultaneously to opposing electrode segments 30, 31, whereby the time for connecting the tissue parts 116 in the case of the example that is schematically represented in FIGS. 1 to 5 can be halved.

After connecting the tissue parts 116, surplus tissue is removed by the cutting device 86. The cutting device 86 is thereby preferably used in a bipolar manner, i.e., the cutting element 88 and the annular electrode 96 are connected to the HF current generator 18 and an HF current for cutting through the tissue is made to pass via the two tissue parts 116. The inclined cutting edge 90 has the effect of generating a defined cutting spark, to be precise in the region in which the distance between the cutting element 88 and the annular electrode 96 is minimal. Starting from this region, the cutting spark then automatically travels around in a circle along the cutting edge 90 in both directions, until the tissue is completely cut through. Using the cutting device 86 in the bipolar operating mode has the advantage in particular that, during the cutting-through, the tissue parts 116 are at the same time also made to coagulate to staunch undesired bleeding directly while cutting through.

After connecting and trimming the tissue parts 116, the instrument 12 can then be withdrawn from the patient's body, for example, from their intestine, by retracting the shaft 24.

Depending on the configuration of the instrument 12, the shaft 24 is preferably of such a length that, during the use of the instrument 12, both the actuating device 76 and the cutting actuating device 98 still protrude out of the patient's body, so that they can be actuated by an operator.

Figure 6:
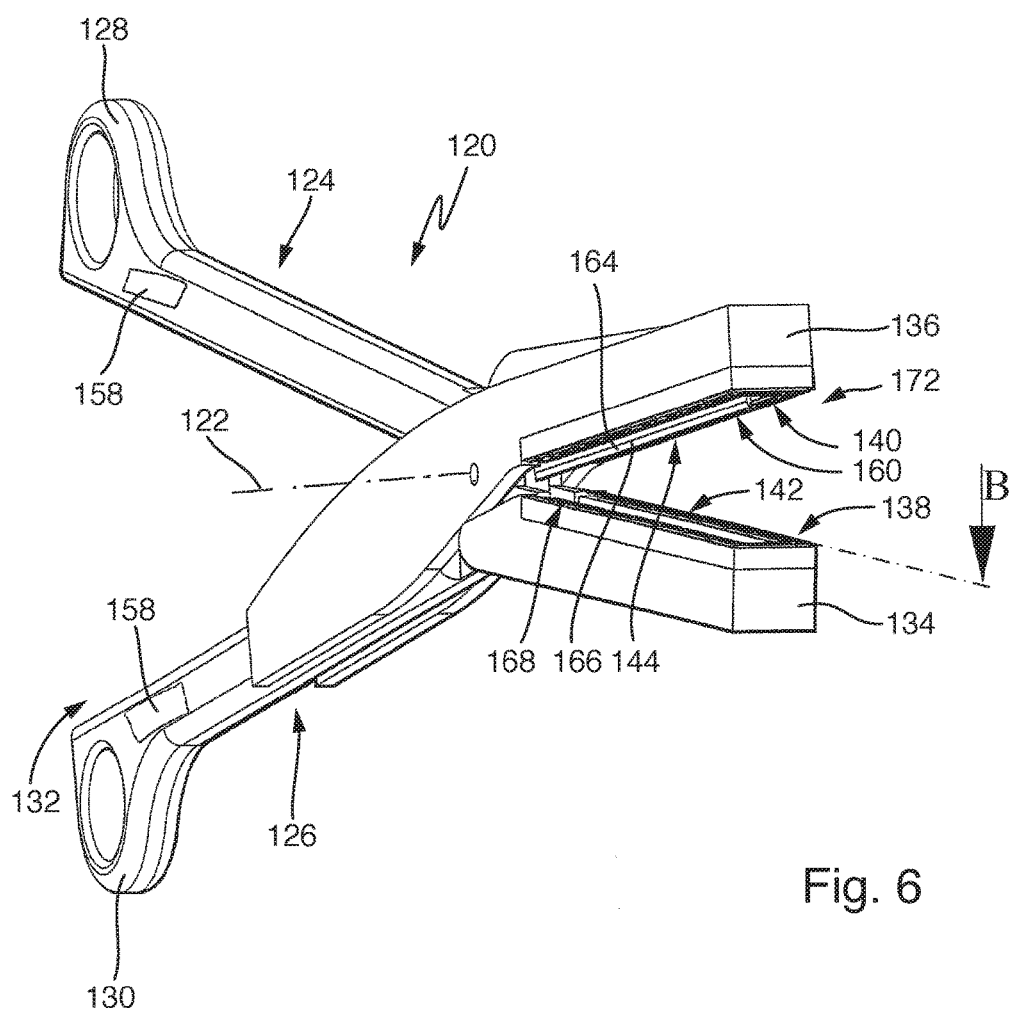
FIG. 6 shows a perspective, schematic view of a second example of a surgical instrument for connecting body tissue parts.
Figure 7:
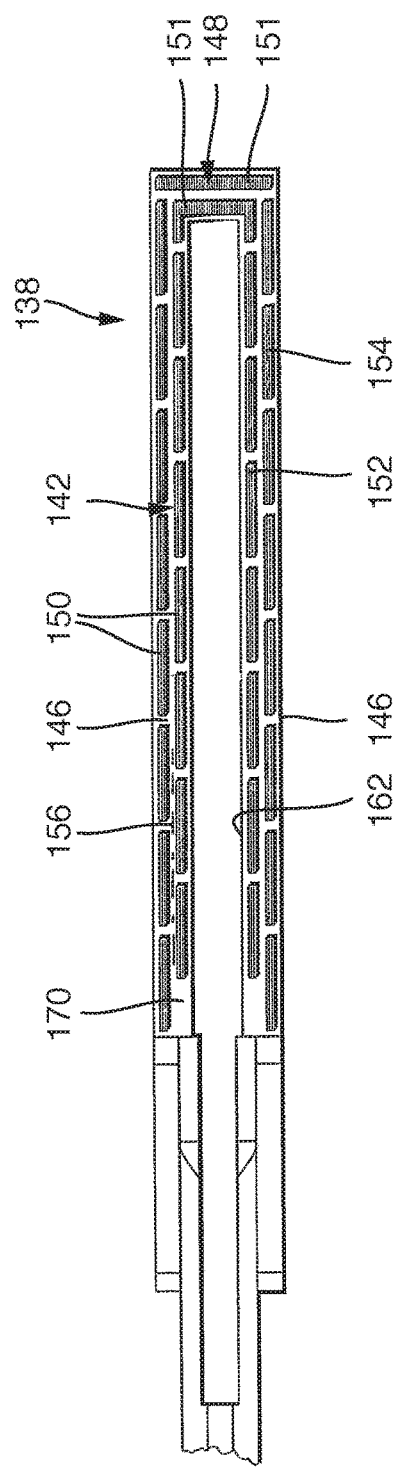
FIG. 7 shows a plan view of a schematically represented tool element area of the instrument from FIG. 6 in the direction of the arrow B.

Alternatively or in addition, instead of the instrument 12, the surgical system 10 may also comprise a surgical instrument that is, for example, in the form of an instrument 120 schematically represented in FIGS. 6 and 7. The instrument 120 comprises two branches 124 and 126, which are mounted on one another such that they can be pivoted in relation to one another about a pivot axis 122. Formed at a proximal end of the branches 124, 126 are finger rings 128, 130, which together define an actuating device 132 for actuating the instrument 120.

Extending from free, distal ends 134 and 136 of the branches 124 and 126, tool elements 138 and 140 are formed on the inner sides of the same, facing one another. The tool elements 138 and 140 are identically formed and, in a coming-together position of the ends 134 and 136, lie opposite one another and, in this position, are at a minimal distance from one another. Each tool element 138, 140 comprises an HF electrode 142, 144, which are formed identically and are of a substantially U-shaped form. Each HF electrode 142, 144 comprises two electrode portions 146, which run parallel to one another and extend in a direction perpendicular to the pivot axis 122, and one electrode portion 148, which runs perpendicularly in relation to the parallel portions and is adjacent to the ends 134, 136.

The construction of the HF electrodes 142, 144 is described in more detail below on the basis of the HF electrode 142, by way of example, in conjunction with FIG. 7.

The HF electrode 142 comprises a total of 30 electrode segments 150, 15 electrode segments in each case being arranged offset in relation to one another in two rows of electrodes 152, 154, parallel to one another along each electrode portion 146, and are electrically insulated from one another. The electrode segments 150 are formed in a straight line and are of a strip-shaped form. They define between them an electrode center line 155, which, in a way corresponding to the form of the HF electrode 142, is likewise of a U-shaped form. In the region of the electrode portion 148, two further electrode segments 151 are arranged, in each case completing the rows of electrodes 152 and 154, respectively, of the electrode portions 146. The electrode segments 150 and 151 are consequently arranged offset in relation to one another in a direction defined by the electrode center line 156.

To be able to apply an HF current to the electrode segments 150, 151, they are arranged in each case to be electrically conducting with an HF terminal 158 in proximal end regions of the branches 124, 126 adjacent to the finger rings 128, 130. The HF terminals 158 may be connected by means of corresponding connecting lines or cables to the HF current generator 18.

On account of the identical formation of the HF electrodes 142 and 144, in the coming-together position electrode segments 150 and 151 of the same size or substantially the same size lie opposite one another and face one another. They form a pair of electrode segments designated overall by the reference sign 168. Altogether, the instrument 120 consequently comprises 32 pairs of electrode segments 168.

The tool elements 138 and 140 also define planar tool element areas 170, which are of a U-shaped form. The electrode segments 150 and 151 do not protrude beyond the tool element area 170.

The instrument 120, formed overall in the form of forceps, may likewise be used for connecting tissue parts, these being held in a clamping manner between the tool elements 138, 140 and then welded or sealed to one another by correspondingly applying current to the electrode segments 150, 151. As described in conjunction with the function of the instrument 12, for this purpose current may be supplied to the electrode segments 150 sequentially, i.e., proceeding along a U-shaped path, after supplying current to one electrode segment 150, the nearest electrode segment 150 of the adjacent row of electrodes 152, 154 is supplied with current, until current has been supplied once to all the electrode segments 150, 151, in this way, a two-rowed connecting line for connecting two tissue parts can be produced. Alternatively, it is also conceivable in the case of the instrument 120 for current to be supplied to two or more electrode segments 150, 151 simultaneously, though preferably electrode segments 150, 151 that are adjacent to one another are not supplied with current simultaneously, but instead at least one, better two or three, electrode segment(s) 150, 151 between electrode segments 150, 151 supplied simultaneously with current remain without current.

The instrument 120 may optionally also comprise a cutting device 160, as schematically represented in FIG. 6. Between the electrode portions 146, a slit 142 is in each case formed on the tool elements 138, 140. In the slit 162 on the branch 126, a cutting element 164 is held with a cutting edge 166 facing in the direction of the slit 162 of the branch 124, and is optionally movable in relation to the tool element 136. Consequently, for example, the tissue held between the tool elements 138 and 140 can already be cut through when the branches 124 and 126 are closed. Optionally, the cutting element 164 may also be used in a monopolar or bipolar manner, it being possible, for example, for the HF electrode 142 to be used as a counterelectrode with respect to the cutting element 164 in the case of bipolar use. In this case, the cutting element 164 is also connected in an electrically conducting manner to a contact of the HF terminals 158.

Represented in FIGS. 8 to 11 is a variant of the instrument 12 which differs by the configuration of the second tool element, which is designated in FIGS. 8 to 11 by the reference sign 16'. In an operating, position, in which it can be brought into the coming-together position described above; the tool element 16' assumes the form of a circular ring. It comprises two circular ring portions 180 and 182, which in each case extend over an angle of approximately 180° with respect to the longitudinal axis 54. Free ends of the circular ring portions 180, 182 are only half as wide as the circular ring portions 180, 182 in the remaining region and serve as bearing blocks 184 and 186. The bearing blocks 184 and 186 are in each case provided with a transverse bore 188 and 190, into which a cylindrical rod 192 is inserted. The bearing blocks 184 lie against the bearing, blocks 186 on the side of the latter that is facing the longitudinal axis 54. The rod 192 is fixed in terms of rotation in the transverse bores 190 of the circular ring portion 182. The transverse bore 188 is dimensioned in its inside diameter such that the circular ring portion 180 is pivotable in relation to the rod 192 about a pivot axis 242 defined by the latter, and consequently in relation to the circular ring portion 182.

The two circular ring portions 180 and 182 are in each case additionally coupled via a rod-shaped link 194 to a holding member 84', which defines a holding member longitudinal axis coinciding with the longitudinal axis 54. By analogy with the holding member 84, the holding member 84' is coupled, or able to be coupled, to the force transmission member 80, and in this way is movable in relation to the shaft 24 in the distal and proximal directions. For the movable articulation of the links 194 on the holding member 84', the latter is provided in the region of its distal end with a slit 204, which extends transversely in relation to a longitudinal axis defined by the rod 192. Formed in this way are two legs 206, which are provided with an in-line transverse bore 208, in which a cylindrical bearing pin 210 is inserted fixedly in terms of rotation. The links 194 are provided at their first ends with a receiving bore 212, through which the bearing in 210 extends and which has an inside diameter to allow a pivoting movement of the links 194 about a pivot axis defined by the bearing pin 210. Approximately from the proximal side of the slit 204, in the holding member 84' there extends further in the proximal direction a longitudinal slit or slot 214, which is passed through by the rod 192. In this way, the rod 192 is displaceable in a defined manner and parallel to itself in a direction parallel to the longitudinal axis 54. A proximal end of the slot 214 forms a proximal end stop for the rod 192; a distal end 218 of the slot 214 forms a distal end stop for the rod 192.

Serving for moving the rod is an actuating mechanism 222, which comprises a sleeve-shaped force transmission element 220, the inside diameter of which is adapted to the outside diameter of the holding member 84' and is consequently displaceable on the holding, member 84' in the distal and proximal directions. Adjacent to its distal end 224, the force transmission element 220 is provided with a bore 226, which the rod 192 passes through. The rod 192 is rotatable in relation to the bore 226. The actuating mechanism 222 may also form part of the actuating mechanism 76 described above. This means that a movement of the rod 192 is also possible, for example, by the pivoting of the actuating members 100 in relation to one another. Alternatively, it would be conceivable to provide a further actuating device, analogous to the actuating device 76, which comprises one or two further actuating members, similar to the actuating members 100 to realize a relative movement between the force transmission member 220 and the holding member 84' in a specific manner.

Arranged on upper sides of the circular ring portions 180 and 182 there are in each case two bearing blocks 228, which are parallel to one another and are provided with bores 230 parallel to the transverse bore 208. Between the bearing blocks 228, a further end of the links 194 is in each case mounted pivotably on the bearing shaft 200 inserted in the bores 230. It is ensured by the described arrangement of the links 194, which may also be referred to as articulating members, that they act with one end on the second tool element 16' at a point of action or articulation, which is at a distance from the pivot axis 242.

Figure 8:
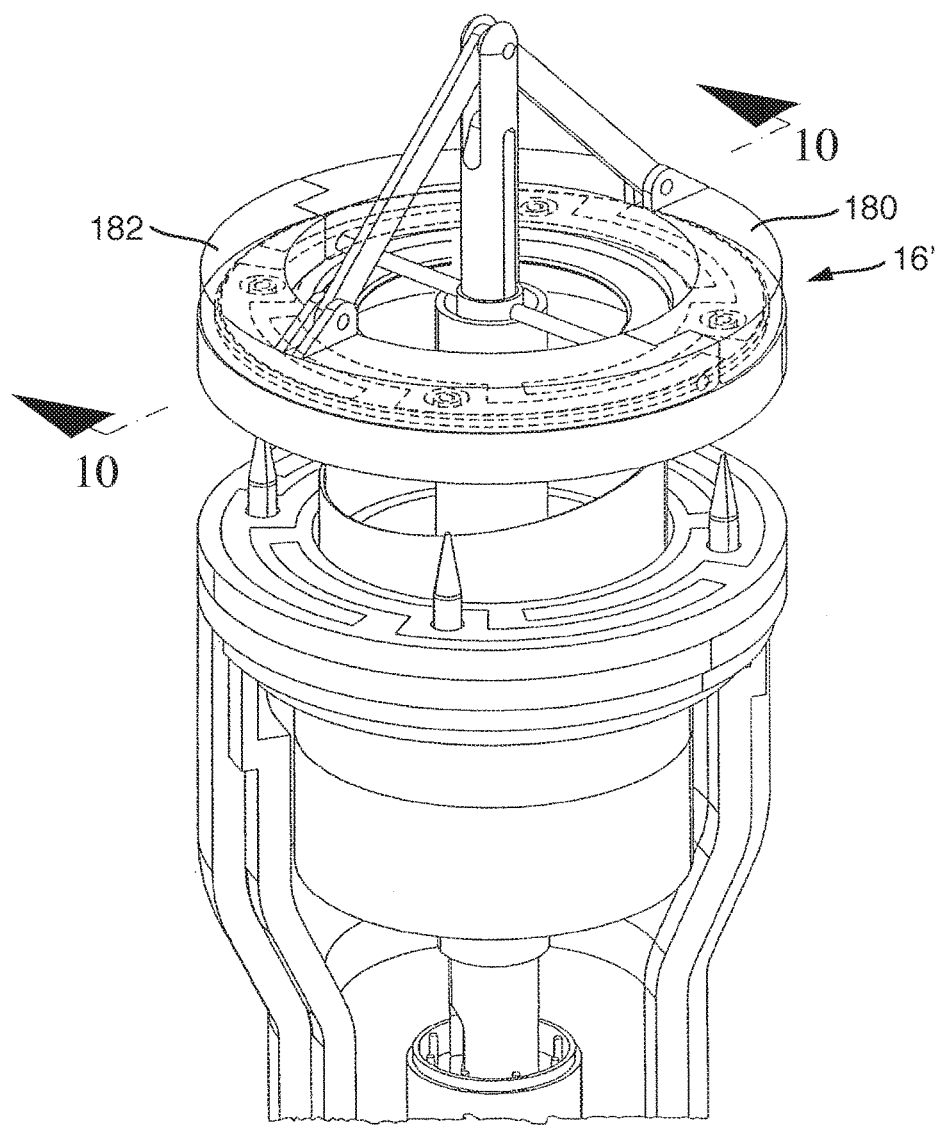
FIG. 8 shows a schematic view similar to FIG. 2 of an alternative configuration of the instrument in a tissue-accepting position.
Figure 9:
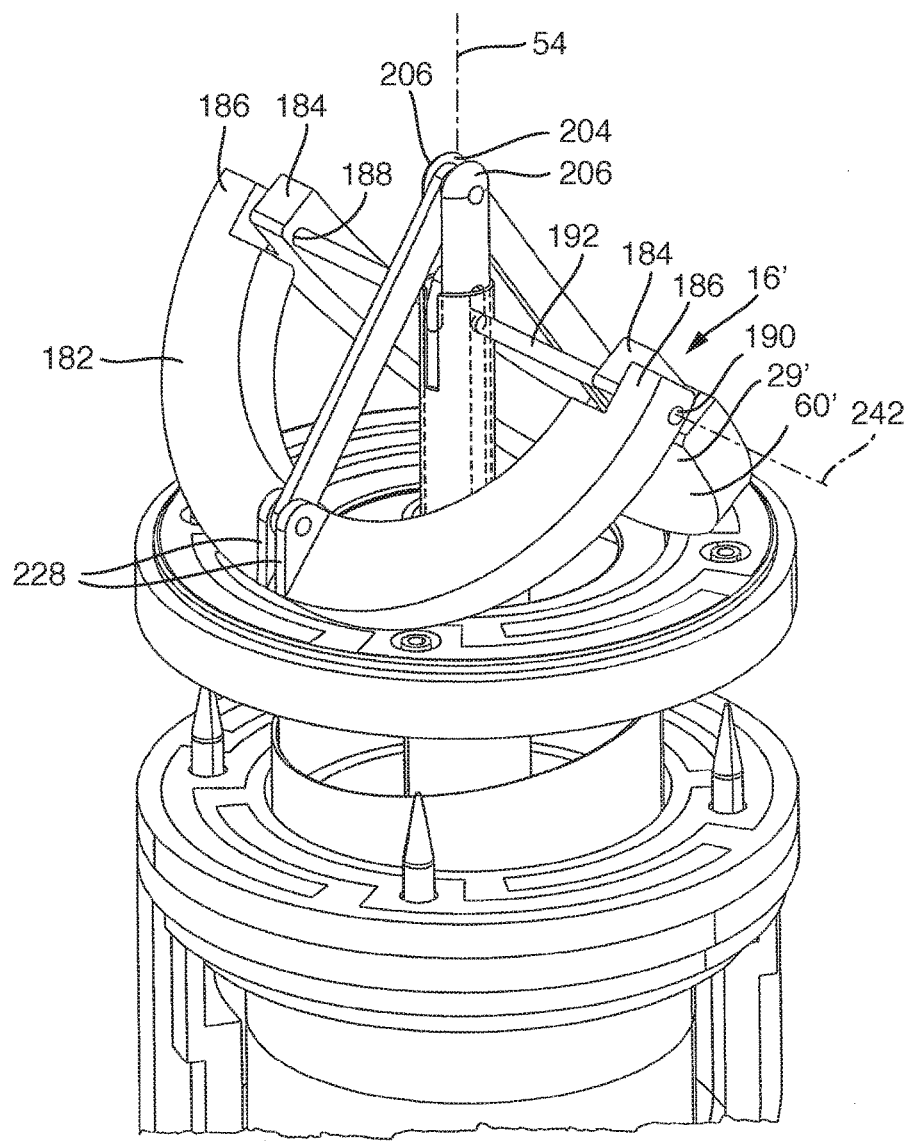
FIG. 9 shows a view corresponding to FIG. 8 of the instrument represented there, with the second tool element partially folded away.
Figure 10:
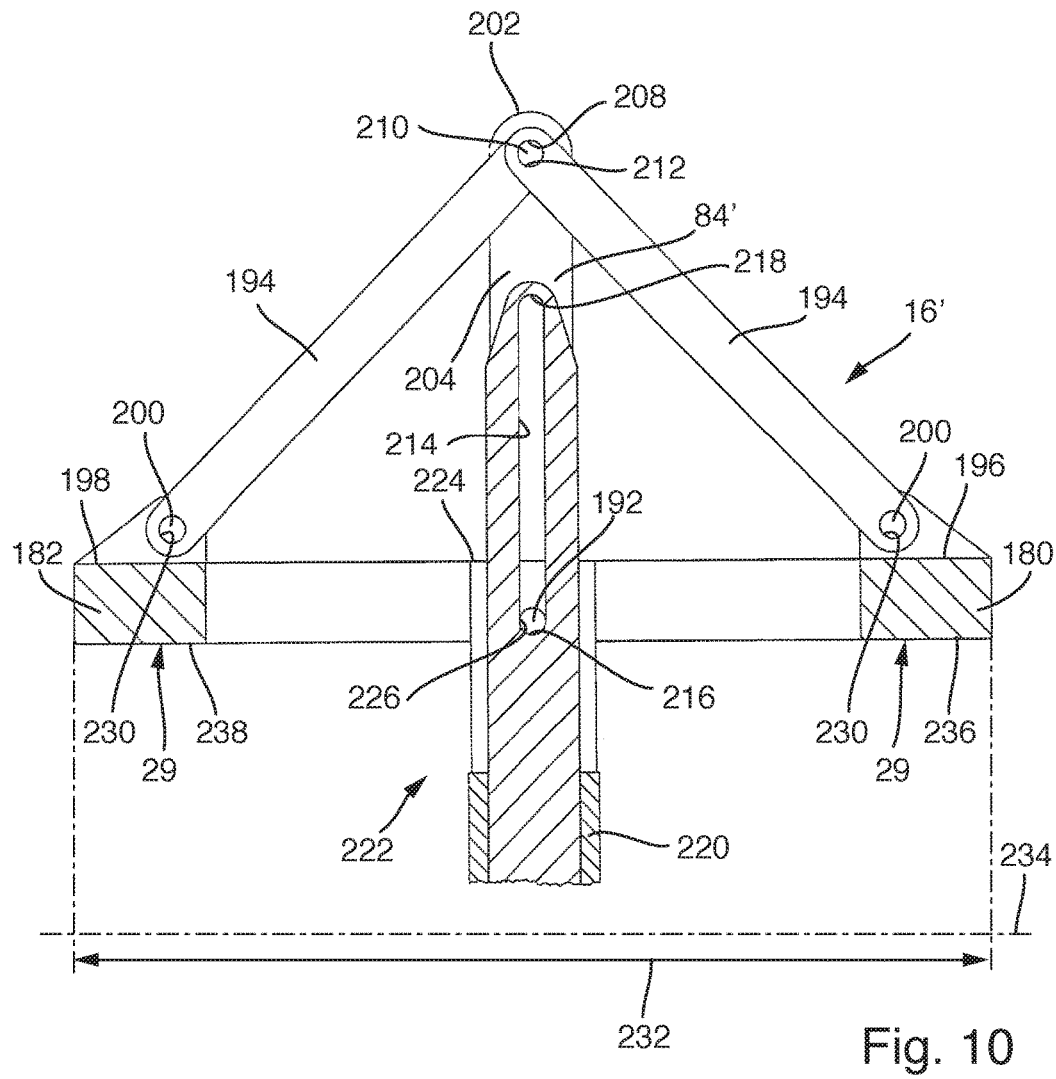
FIG. 10 shows a sectional view along the line 10-10 in FIG. 8.
Figure 11:
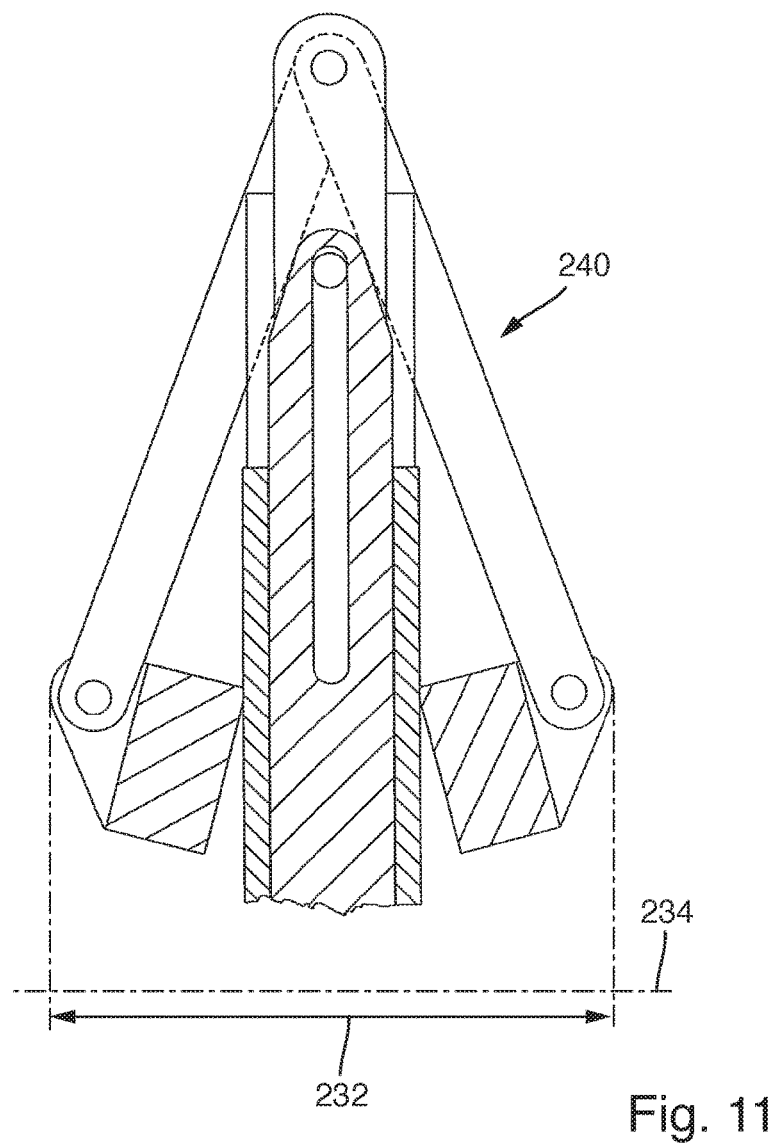
FIG. 11 shows a schematic sectional view similar to FIG. 10 of the folded-together, second tool element in a position such as that represented in FIG. 9.
Figure 12:
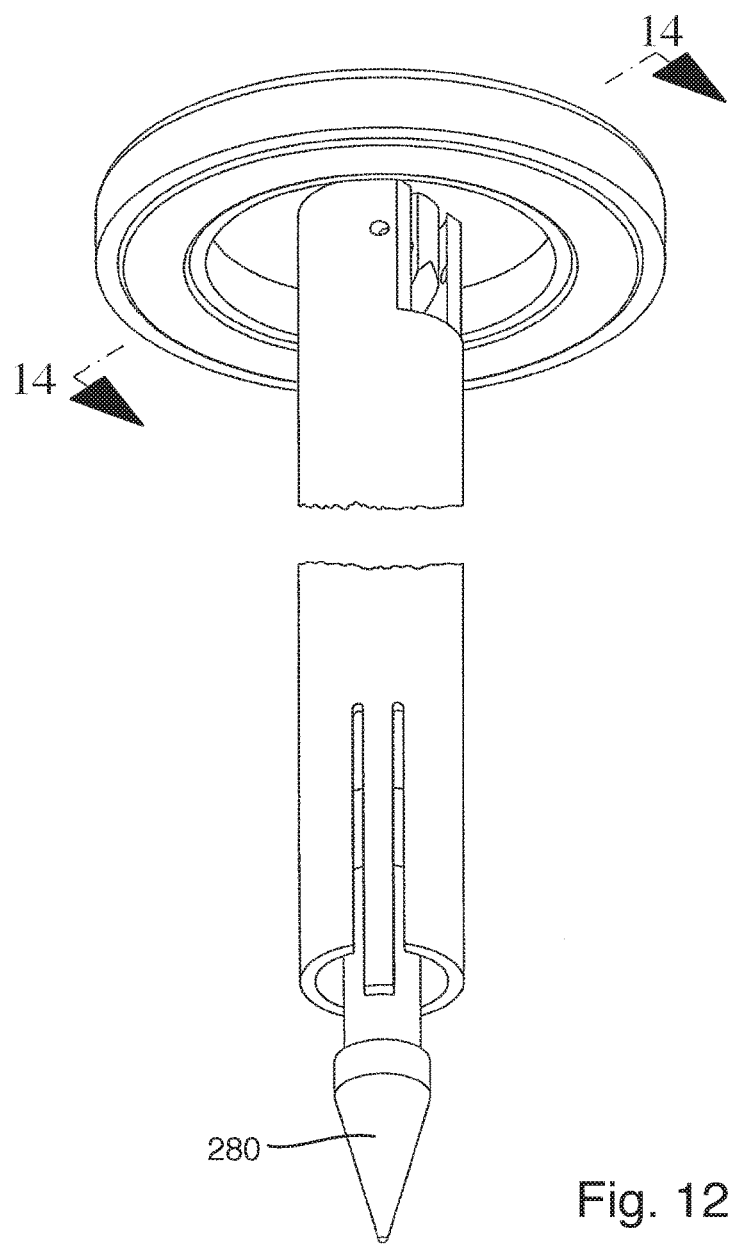
FIG. 12 shows an alternative example of a second tool element in a perspective schematic representation.
Figure 13:
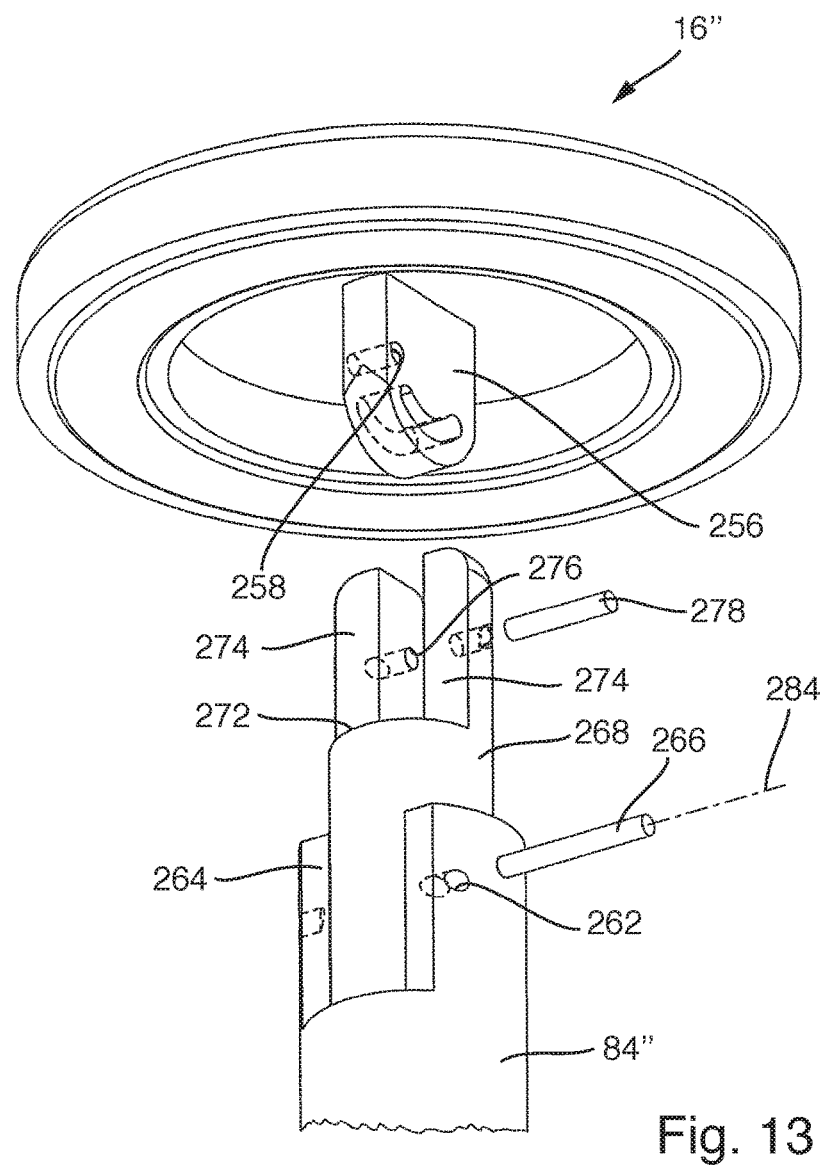
FIG. 13 shows an exploded representation of part of the second tool element represented in FIG. 12.

With the actuating mechanism 222, the second tool element 16' can be brought from the already mentioned operating position, which is schematically represented in FIGS. 8 and 10, into the removal position, which is represented by way of example in FIG. 11, FIG. 9 schematically represents an intermediate position, that is to say a position between the operating position and the removal position. As can easily be seen by comparing the two FIGS. 10 and 11, a zone of a perpendicular projection of the second tool element 16' onto a projection plane 234, which runs perpendicularly in relation to the longitudinal axis 54, that is in relation to the shaft direction in the region of the second tool element 16', is smaller in the removal position than in the operating position. This is achieved by a movement of the sleeve-shaped force transmission element 220 from the operating position, in which the rod 192 strikes the proximal end 216 and undersides 236 and 238 of the circular ring portions 180 and 182 extend parallel to the projection plane 234. If the force transmission element 220 is moved in the distal direction, the rod 192 is forcibly guided in the distal direction in the slot 214. As a result of the articulated connection of the circular ring portions 180 and 182 in relation to one another and by the two links 194 with the holding member 84', the circular ring portions 180 and 182 pivot about the pivot axis 242 in the direction towards the longitudinal axis 54. The second tool element 16' is folded together in this way. Therefore, a folding mechanism 240 for transferring the second tool element 16' from the operating position into the removal position is funned by the articulated arrangement of the circular ring portions 180 and 182 by the links 194.

Not mentioned so far is the configuration of the undersides 236 and 238 of the second tool element. These may either comprise a single, substantially continuous annular electrode, which forms a single counterelectrode with respect to the HF electrode 28 of the first tool element 14. Alternatively, by analogy with the HF electrode 29, an HF electrode with two or more electrode segments 31 may also be formed on the undersides 236 and 238, preferably in a way corresponding to the HF electrode 29. This then allows in the operating position a connecting of tissue parts 116 to be performed in the way described above. After the connecting of the tissue parts, the folding mechanism 240 may then be actuated, for example, by appropriate actuation of the described actuating mechanism 222, whereby the holding member 84' is moved in the distal direction. If the force transmission element 220 is, for example, arranged immovably in relation to the shaft 24, the second tool element 16' may be automatically folded together when there is a movement in the distal direction of the force transmission element 80. As a result of the significantly reduced area requirement in the removal position, the second tool element can be led through a connecting site formed by the connecting of the tissue parts 16 during the removal of the instrument 12, doing so without stretching the connecting site, which is much more tolerable than leading the second tool element through the connecting site in the operating position.

It goes without saying that electrically conducting connections of the electrode 29 to the HF terminal contacts 50, for example, via the links 94 and the holding member 84', can be led to the HF terminal contacts 50 in the proximal end region of the shaft 24.

A further variation of a second tool element is designated in FIGS. 12 to 15 overall by the reference sign 16". It takes the place, for example, of the tool elements 16 and 16' described above of the instrument 12.

The second tool element 16" is substantially in the form of a plate, with a slightly convexly curved outer side 250 facing in the distal direction.

Formed on an underside of the second tool element 16" is an annular groove 252, which is open facing in the proximal direction. Formed centrally in the middle is a substantially circular depression 254, arranged in which is a substantially cuboidal bearing projection 256, which is formed protruding coaxially in relation to the longitudinal axis 54 in the proximal direction from the underside of the second tool element 16". The bearing projection 256 is provided with a transverse bore 258, which is skewed with respect to the longitudinal axis 54. Also formed on the bearing projection 256 is a curved guiding slit 260, which is convexly curved facing in the proximal direction. A proximal end of the bearing projection 256 has a rounded-off outer contour.

The second tool element 16" is pivotably mounted on a sleeve-shaped holding member 84". For this purpose, the holding member 84" is provided with a transverse bore 262, which passes through a wall 264 of the holding member 84" at two locations. A bearing pin 266 is inserted fixedly in terms of rotation in the transverse bore 162. At the same time, it passes through the transverse bore 258 such that the bearing projection 256 is pivotable about a pivot axis 284 defined by the bearing pin 266. To be able to actuate a folding mechanism 270 that is also provided in the case of the second tool element 16", a force transmission element 268 is provided, substantially of a rod-shaped form and passing through the holding member 84" coaxially in relation to the longitudinal axis 54. From a distal-side end face 272 of the force transmission element 268, two bearing legs 274 are arranged parallel to one another and protruding in the distal direction, and are in each case passed through by an in-line bore 276. Inserted in a rotationally fixed manner in the bores 276 is a further bearing pin 278, which is oriented parallel to the bearing pin 266. An outside diameter of the bearing pin 278 is dimensioned such that it can pass through the guiding slit 260 and can be moved in relation thereto.

A proximal end 280 of the force transmission element 268 is preferably able to be coupled to the force transmission member 80, so that, as a result of a movement of the same, the second tool element 16" can also be moved.

Inserted in the annular groove 252 is a ring-shaped electrode element 282, which preferably comprises an HF electrode 29 of the form described above and is not represented in detail in FIGS. 12 to 15 for the sake of overall clarity. Alternatively, a simple, continuous annular electrode may also be formed on the electrode element 282.

Figure 14:
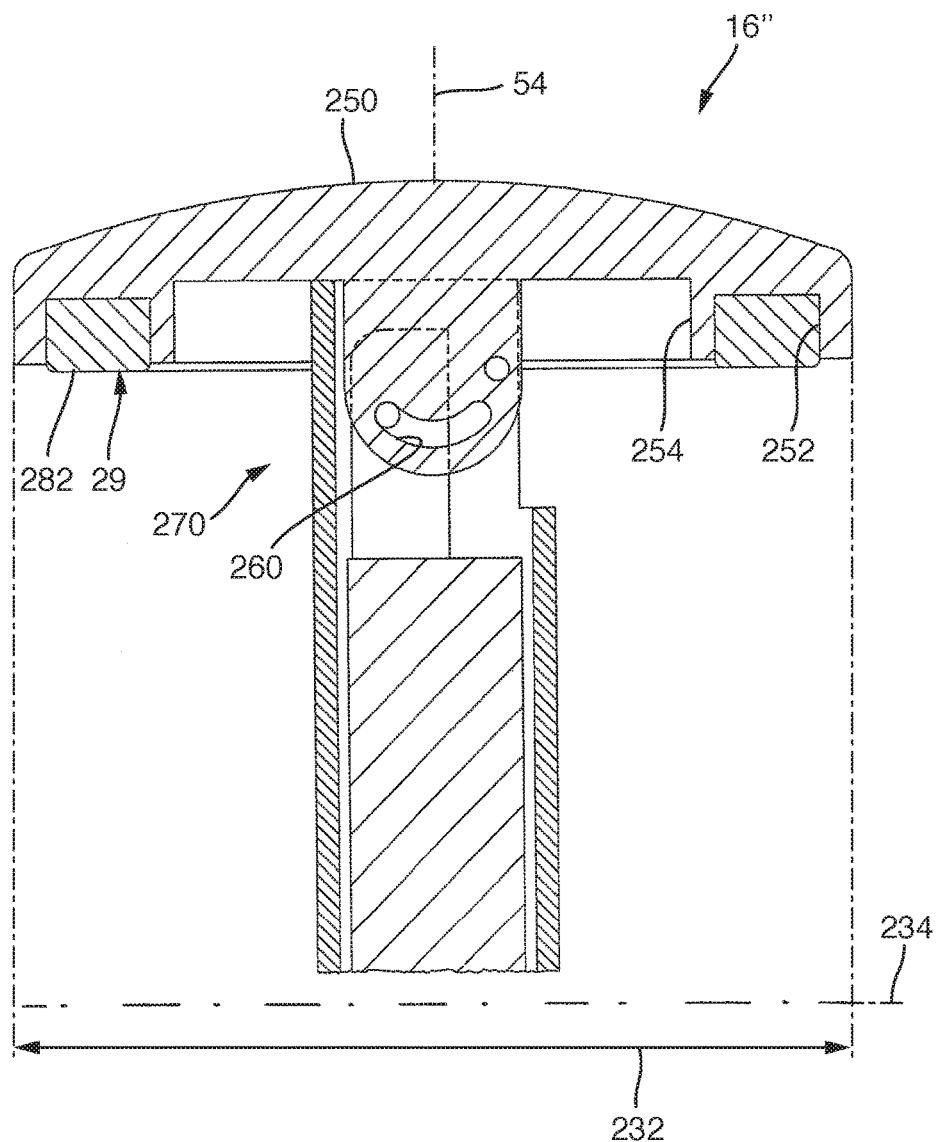
FIG. 14 shows a sectional view along line 14-14 in FIG. 12.
Figure 15:
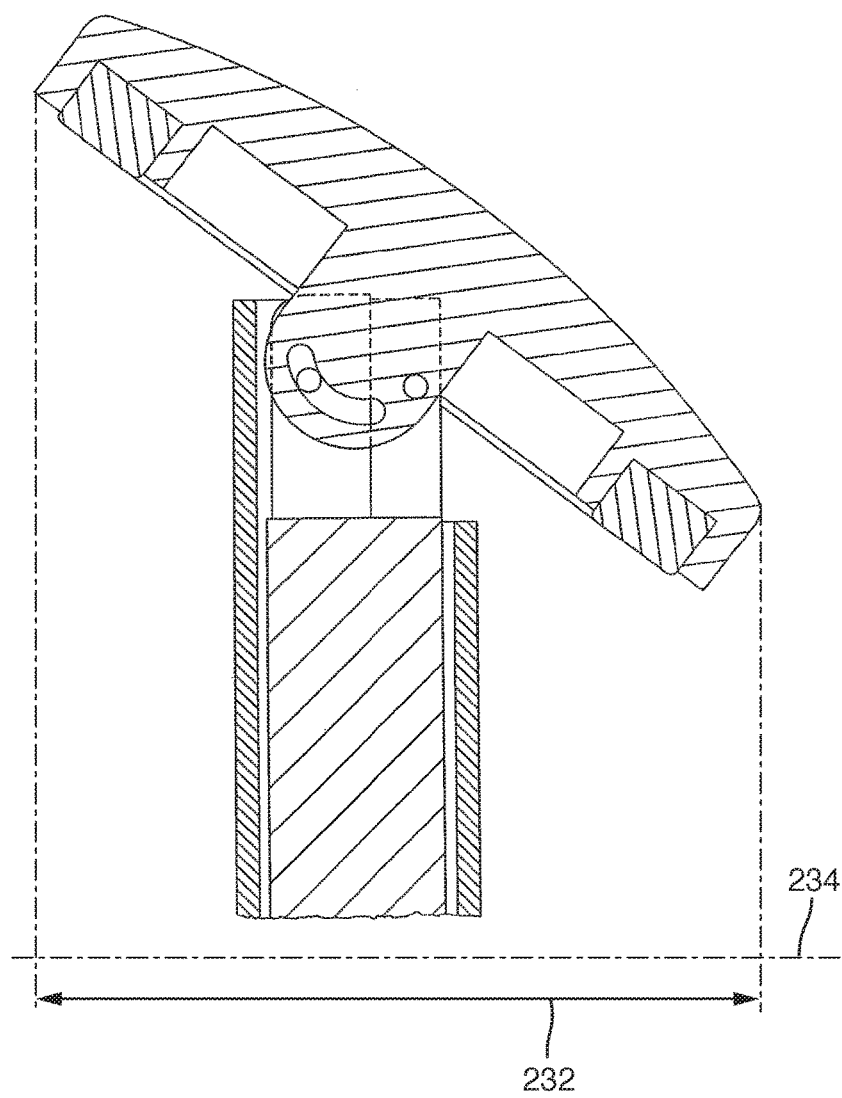
FIG. 15 shows a schematic sectional view analogous to FIG. 14 of the example represented there, with the second tool element partially folded away.
Figure 16:
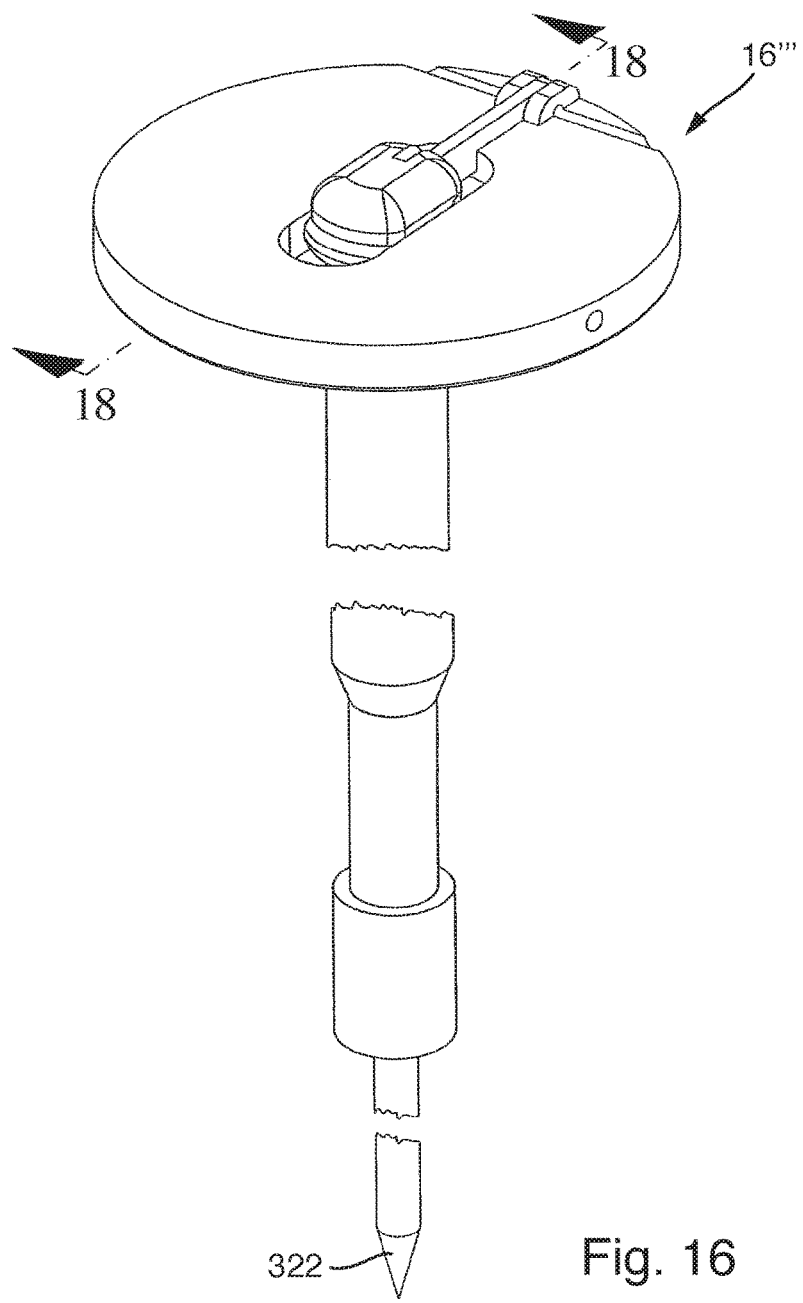
FIG. 16 shows a perspective schematic representation similar to FIG. 12 of a further example of a second tool element.
Figure 17:
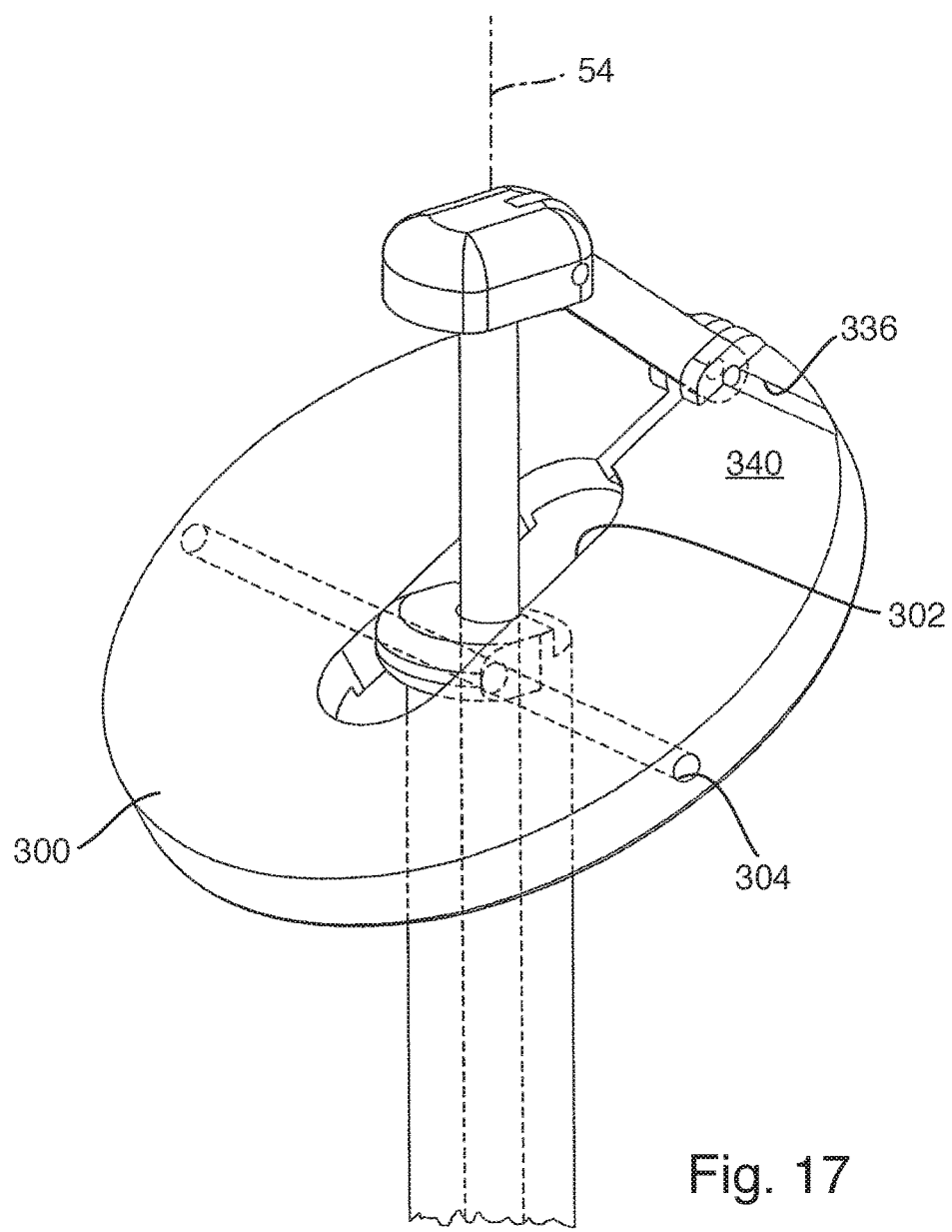
FIG. 17 shows an enlarged representation of the second tool element from FIG. 6 in a partially inclined position.
Figure 18:
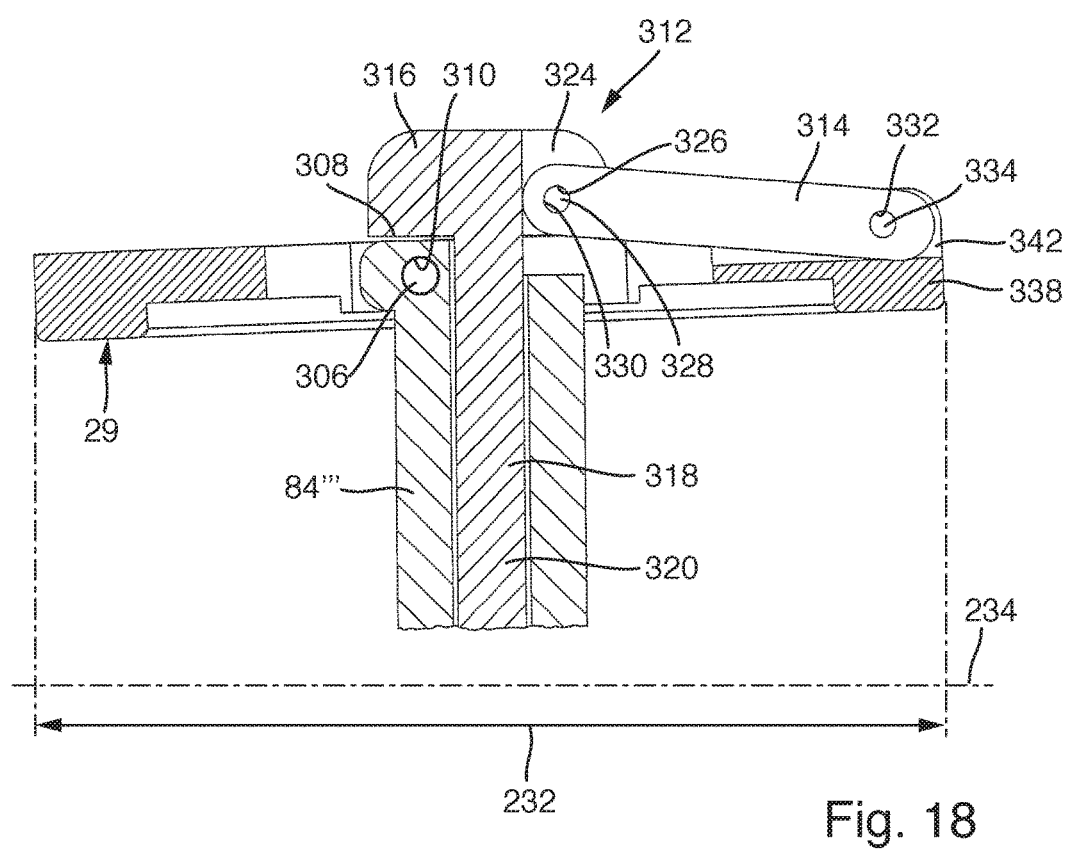
FIG. 18 shows a sectional view along the line 18-18 in FIG. 16.
Figure 19:
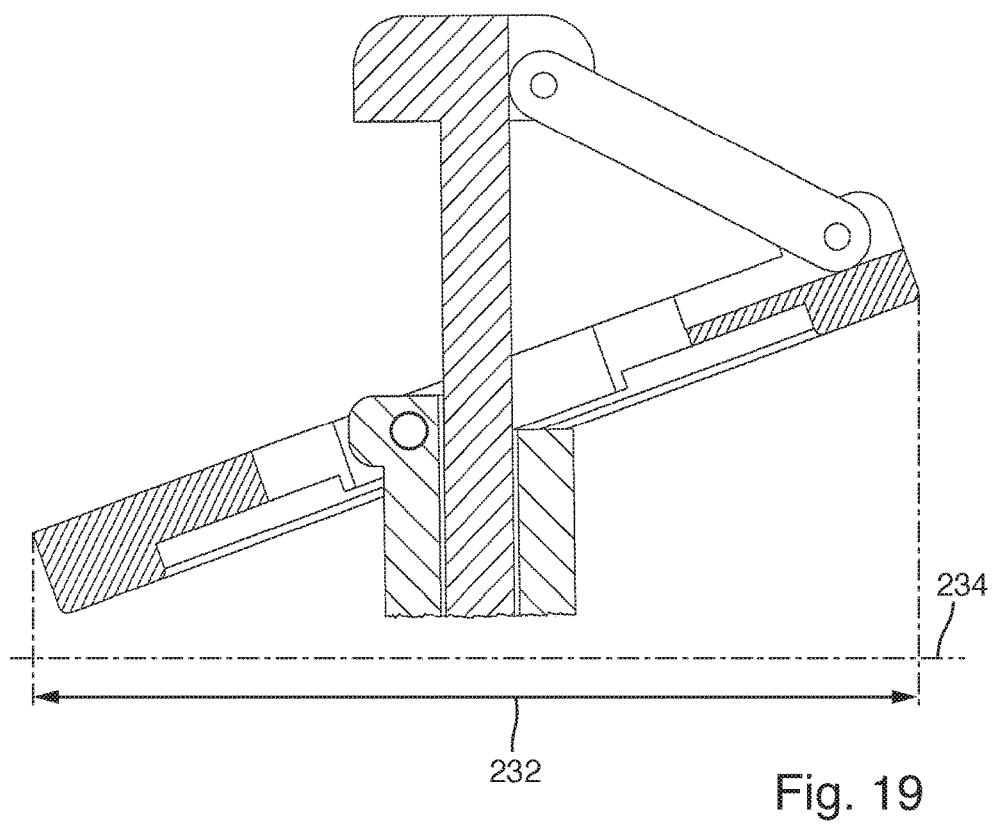
FIG. 19 shows a view analogous to FIG. 18 with a partially inclined second tool element, in a position such as that represented in FIG. 17.

To transfer the second tool element 16" from the operating position into the removal position, the force transmission element 268 is moved in the distal direction. The specially curved guiding slit 260 has the effect that the bearing; pin 278 is forcibly guided in it and consequently brings about a forcibly guided pivoting of the second tool element 16" about the pivot axis 284. Thus, the second tool element 16" can substantially be pivoted by almost 90°, so that also in the case of this variation of the tool element 16" a perpendicular projection 232 of the same onto the projection plane 234 is smaller in the removal position than in the operating position, as schematically represented in FIGS. 14 and 15. In this way, overstretching of the connecting site between the tissue parts 116 to be connected to one another is avoided in the removal position during the removal of the instrument 12.

A second tool element, provided overall with the reference sign 16', is represented in FIGS. 16 to 19. It may be used on the instrument 12 in place of the previously described second tool elements 16, 16' and 16".

The second tool element 16''' is substantially in the form of a plate and comprises a disc 300. This is provided in its center with a transversely running, elongated oval slit 302. A bore 304 passes through the disc 300, offset laterally somewhat in relation to the center point thereof, which lies in the region of the slit 302. Inserted fixedly in terms of rotation in the bore is a bearing pin 306, which likewise passes through the slit 302. In the region of the slit 302, a distal end of a holding member 84''', which is in the form of a sleeve, protrudes in. The holding member 84''' is provided on the proximal side from its end 308 with a bore 310, the inside diameter of which is adapted to the outside diameter of the bearing pin 306 such that the bearing pin 306 is rotatable in relation to the bore 304 in the latter. This then makes it possible overall for the plate 300 to be pivoted about a longitudinal axis 344 defined by the bearing pin 306.

Serving for the forcibly actuated pivoting of the disc 300 is a folding mechanism 312, which couples the disc 300 in an articulated manner to a distal end 316 of a force transmission element 318 by a link 314. The force transmission element 318 has an elongated, rod-shaped portion 320, the proximal end 322 of which can be coupled to the force transmission member 80. The end 316 is bent with respect to the portion 320 in the form of a head and is shaped in a virtually cuboidal manner. Formed on one side of the same is a laterally open slit 324. Also provided is a transverse bore 326, which passes transversely through the slit 324. Inserted fixedly in terms of rotation in the transverse bore 326 is a bearing pin 328. The rod-shaped link 314 is likewise provided with a bore 330 and is pivotably mounted on the bearing pin 328. Adjacent to an opposite end of the link 314, a further bore 323 is provided. It serves for mounting the link 314 on a further bearing pin 334. This pin is inserted in a further bore 336 of the disc 300. The bore 336 is oriented parallel to the bore 304 and arranged outside the slit 302 adjacent to a periphery 338 of the disc 300, to be precise opposite the bore 304 with respect to the longitudinal axis 54. Machined on an upper side 340 of the disc 300, extending from the periphery 338, is a groove 342, seated in which is the end of the link 314 with its bore 332. In this way, the link 314 is mounted in an articulated manner on the bearing pin 334. Consequently, the link 314 acts with one end on the second tool element 16''' at a point of action or articulation which is at a distance from the pivot axis 344.

The folding mechanism 312 is actuated by the force transmission element 318 being moved in the distal direction. This has the consequence that the link 314 is angled away in relation to the disc 300. The further the force transmission member 318 is moved in the distal direction, the further the link 314 thereby pulls the region of the disc 300 on which the groove 342 is provided in the distal direction. In an extreme position, the disc 300 is then aligned almost parallel to the longitudinal axis 54. Overall, it is consequently also possible in the case of the second tool element 16''' to realize a removal position in which a perpendicular projection 232 of the same onto the projection plane 224, which runs perpendicularly to the longitudinal axis 54, is smaller than in the operating position.

An HF electrode 29 in a form as described above in the case of the second tool element 16 may likewise be arranged or formed on the second tool element 16'''. Alternatively, it is also conceivable to provide a closed, ring-shaped electrode, which is not divided into electrode segments. In a way similar to the second tool element 16" comprising the electrode element 282, electrode elements may likewise be provided in the case of the second tool elements 16 and 16''', for example, in the form of the electrode element 282 or else the electrode element 52.

As already mentioned above in conjunction with the second tool element 16', the HF electrodes provided on the second tool elements 16" and 16'" may be connected to the HF terminal contacts 50 in the customary way by providing corresponding electrically conducting connections on the instrument 12.

Figure 20:
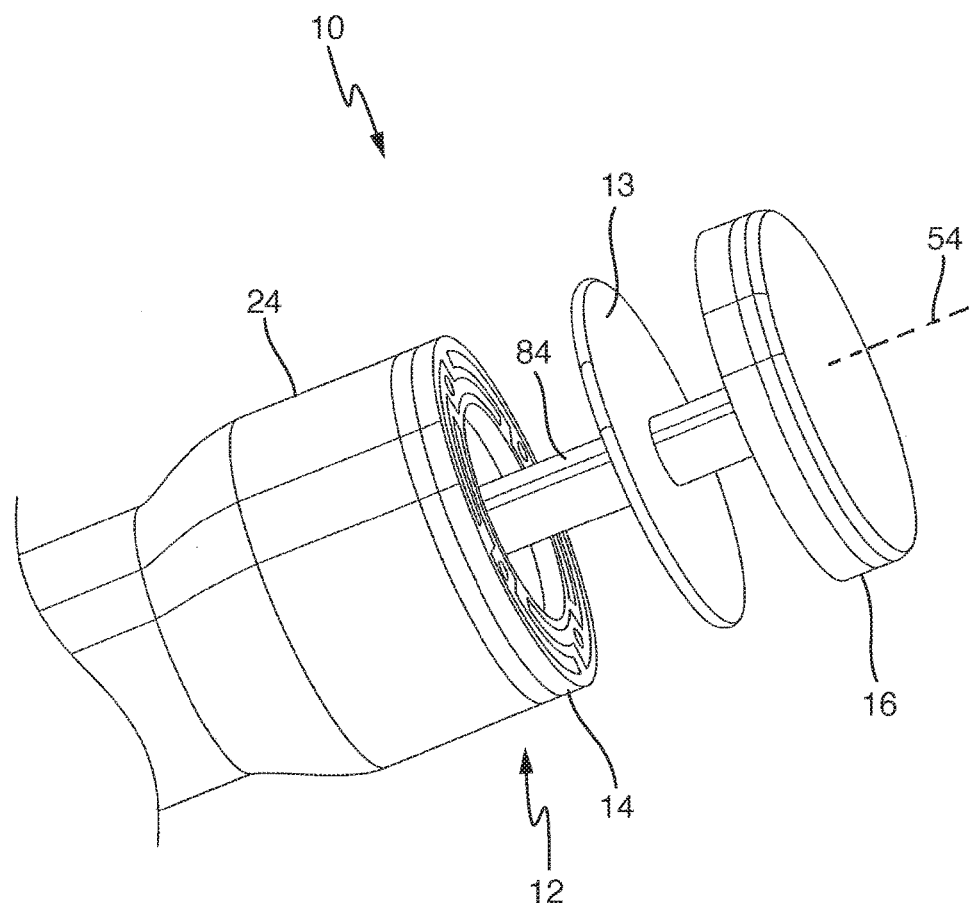
FIG. 20 shows a view of the surgical instrument.

FIG. 20 shows an example of a surgical system 10. The system 10 comprises a surgical instrument 12 and a medically compatible material 13, assisting or conducive to the connection of tissue, in the form of a disc, which is preferably in the form of a circular ring. The surgical instrument 12 is an instrument such as that described in more detail in FIGS. 1 to 5. However, it may similarly be preferred that, in place of the surgical instrument 12 represented, the surgical system 10 comprises one of the variations of the instrument 12 that are represented in FIGS. 6 to 19.

The disc 13 is preferably formed from lyophilized collagen. To achieve greater connecting strengths between the tissue parts 116 to be connected, it may be preferred if the disc 13 comprises a fraction of an organic salt, such as, for example, sodium chloride, potassium chloride, barium chloride, magnesium chloride, calcium chloride or mixtures thereof. More preferably, the collagen is collagen of type I.

The disc 13 has a hole, which is formed approximately in the middle and the diameter of which corresponds approximately to the outside diameter of the holding member 84, which at its proximal end is preferably connected immovably to the second tool element 16. The distal end of the holding member 84 can consequently be led snugly through the hole in the disc 13 and the disc 13 itself can be moved along the holding member 84, in particular in the direction of the proximal end thereof.

Once the distal end of the holding member 84 has been led through the hole in the disc 13, the holding member 84 can be inserted with its distal end into a force transmission member 80 movably mounted in the interior of the shaft 24. For this purpose, as already described in detail above, the force transmission member 80 may have at its distal end a receptacle 82 in the form of a blind hole, in which the holding member 84 can be inserted and can be fixed.

When producing an end-to-end anastomosis of two tubular tissue parts 116, for example, of the intestine, free ends of the tissue parts 116 are brought together, so that they are lying with their free ends facing in the direction of the longitudinal axis 54 and flat against one another in an annular manner, the one free end being located between the first tool element 14 and the disc 13 and the second free end being located between the disc 13 and the second tool element 16. In this way, the tissue parts 116, together with the disc 13, can be held against one another in a sandwich-like structure in a clamping manner between the tool elements 14, 16 in the tissue-accepting position.

The further procedure corresponds to the procedure already described in detail elsewhere. After the connecting of the tissue parts 116 and the disc 13, surplus tissue and the part of the disc 13 that was not included in the sealing process are removed by means of the cutting device 86.

The invention claimed is:

1. A surgical system that connects biological tissue comprising:
   a) a surgical instrument with two tool elements movable in relation to one another and each comprising an electrode, wherein the electrodes define a minimum distance from one another, lie opposite one another and face one another at a position where the tool elements are adjacent to each other, and
   b) a medically compatible material assisting connection of the tissue, wherein at least one of the electrodes comprises at least two contiguous electrode segments, at least one electrode segment has a first electrode segment portion which is part of a first row of electrodes, a second electrode segment portion which is part of a second row of electrodes, and each electrode segment connects in an electrically conducting manner to a terminal contact arranged in a connecting region between the electrode segment portions.

2. The surgical system according to claim 1, wherein the medically compatible material comprises a naturally occurring material in natural tissues.

3. The surgical system according to claim 1, wherein the medically compatible material originates from a biological tissue selected from the group consisting of oesophagus, skin, fascia, pericardium, ureter, tendons, ligaments and combinations thereof.

4. The surgical system according to claim 1, wherein the medically compatible material comprises a connective tissue protein or an extracellular protein.

5. The surgical system according to claim 1, wherein the medically compatible material comprises a protein selected from the group consisting of collagen, gelatin, elastin, reticulin, laminin, fibronectin, fibrillin, albumin, peptide fragments thereof, natural polyamino acids, synthetic polyamino acids, derivatives thereof, salts thereof and combinations thereof.

6. The surgical system according to claim 1, wherein the medically compatible material comprises fibrillary collagen selected from the group consisting of type I, II, III, V and VI collagen and mixtures thereof.

7. The surgical system according to claim 1, wherein the medically compatible material is formed such that it is transferable between the two tool elements.

8. The surgical system according to claim 1, wherein the medically compatible material is applicable to a tool element area of at least one of the two tool elements.

9. The surgical system according to claim 1, wherein the medically compatible material is ring-shaped, plate-shaped, disc-shaped, strip-shaped or U-shaped.

10. The surgical system according to claim 1, wherein the medically compatible material is a spray-bonded nonwoven, a foam, a sponge or a membrane.

11. The surgical system according to claim 1, wherein the medically compatible material further comprises additives comprising sodium chloride, potassium chloride, barium chloride, magnesium chloride, calcium chloride, sodium phosphate, potassium phosphate, barium phosphate, magnesium phosphate, calcium phosphate, mixed phosphates thereof or combinations thereof.

12. The surgical system according to claim 11, wherein the additive comprises a proportion of 0.1% by weight to 20% by weight, based on the total weight of the medically compatible material.

13. The surgical system according to claim 1, wherein the medically compatible material is spatially or physically separate from the surgical instrument.

14. The surgical system according to claim 1, wherein the tool elements are pivotable and/or displaceable in relation to one another.

15. The surgical system according to claim 1, further comprising contact members facing in a direction of second tool element and protruding from a shaft of the surgical instrument and/or from a first tool element in a direction of the second tool element, which members can be brought into electrically conducting contact with the electrode segments of the second tool element in a tissue-connecting position and are at a distance from the electrode segments of the second tool element in a tissue-accepting position.

16. The surgical system according to claim 2, wherein the instrument comprises an HF cutting element to cut through tissue.

17. A surgical system that connects biological tissue comprising:
- a) a surgical instrument with two tool elements movable in relation to one another and each comprising an electrode, wherein the electrodes define a minimum distance from one another, lie opposite one another and face one another at a position where the tool elements are adjacent to each other, and
- b) a medically compatible material assisting connection of the tissue, wherein
  1) at least one of the electrodes is divided into at least two electrode segments, the at least two electrode segments are electrically insulated from one another, each of the tool elements define a tool element area, and each electrode forms a part of the tool element area of its respective tool element,
  2) the at least two electrode segments are arranged next to one another and define at least two rows of electrodes,
  3) at least one electrode segment has a first electrode segment portion which is part of a first row of electrodes, and a second electrode segment portion which is part of a second row of electrodes, and
  4) the electrode, which can be fed with current in segments, defines an electrode center line, and electrode segments adjacent to one another are arranged offset to one another in a direction defined by the electrode center line such that the sum of the lengths of all electrode segments is greater than the electrode length, and wherein each electrode segment connects in an electrically conducting manner to a terminal contact arranged in a connecting region between the electrode segment portions.

* * * * *